(12) United States Patent
Comee et al.

(10) Patent No.: US 12,011,144 B2
(45) Date of Patent: Jun. 18, 2024

(54) DEVICES, SYSTEMS, AND METHODS FOR FLUID CONTROL IN ENDOSCOPE SYSTEMS

(71) Applicant: Boston Scientific Scimed, Inc., Maple Grove, MN (US)

(72) Inventors: Shaun D. Comee, Fiskdale, MA (US); Nathan T. Cummings, Worcester, MA (US); Paula R. Limberg, Northborough, MA (US); Laura E. Richards, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 112 days.

(21) Appl. No.: 17/208,794

(22) Filed: Mar. 22, 2021

(65) Prior Publication Data
US 2021/0298572 A1 Sep. 30, 2021

Related U.S. Application Data

(60) Provisional application No. 62/994,021, filed on Mar. 24, 2020, provisional application No. 62/994,019,
(Continued)

(51) Int. Cl.
*A61B 1/00* (2006.01)
*A61B 1/015* (2006.01)
(Continued)

(52) U.S. Cl.
CPC .......... *A61B 1/00068* (2013.01); *A61B 1/015* (2013.01); *A61B 1/12* (2013.01);
(Continued)

(58) Field of Classification Search
CPC ............ A61B 1/00068; A61B 1/00082; A61B 1/00091; A61B 1/00094; A61B 1/00119;
(Continued)

(56) References Cited

U.S. PATENT DOCUMENTS 4,061,250 A * 12/1977 Tada ................... B05B 11/1014
251/321
4,694,821 A * 9/1987 Kondo ............... A61B 1/00068
600/158
(Continued)

FOREIGN PATENT DOCUMENTS

EP 2431062 A1 3/2012
EP 2878252 A1 6/2015
(Continued)

OTHER PUBLICATIONS

International Search Report and Written Opinion for the International Patent Application No. PCT/US2021/023478, dated Jun. 10, 2021, 49 pages.
(Continued)

*Primary Examiner* — Ryan N Henderson
(74) *Attorney, Agent, or Firm* — Seager, Tufte & Wickhem, LLP

(57) ABSTRACT

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve control motions. In one or more embodiments, the valve sets and/or valve interface mechanisms may be disposable.

6 Claims, 37 Drawing Sheets

Related U.S. Application Data filed on Mar. 24, 2020, provisional application No. 62/994,015, filed on Mar. 24, 2020, provisional application No. 62/994,024, filed on Mar. 24, 2020, provisional application No. 62/994,008, filed on Mar. 24, 2020, provisional application No. 62/994,018, filed on Mar. 24, 2020.

(51) Int. Cl.
  *A61B 1/12* (2006.01)
  *F16K 21/20* (2006.01)
  *A61B 1/018* (2006.01)

(52) U.S. Cl.
  CPC .......... *F16K 21/20* (2013.01); *A61B 1/00082* (2013.01); *A61B 1/018* (2013.01)

(58) Field of Classification Search
  CPC . A61B 1/00128; A61B 1/00137; A61B 1/015; A61B 1/018; A61B 1/12; A61B 1/126; A61B 1/127; F16K 21/20
  See application file for complete search history.

(56) References Cited

U.S. PATENT DOCUMENTS

| | | | | |
|---|---|---|---|---|
| 4,800,869 | A * | 1/1989 | Nakajima | A61B 1/00068 600/158 |
| 6,334,844 | B1 * | 1/2002 | Akiba | A61B 1/00068 600/156 |
| 6,346,075 | B1 | 2/2002 | Arai et al. | |
| 8,568,303 | B2 * | 10/2013 | Yamane | A61B 1/12 600/156 |
| 2010/0049001 | A1 * | 2/2010 | Yamane | A61B 1/015 600/159 |
| 2011/0208003 | A1 * | 8/2011 | Yamane | A61B 1/12 600/159 |
| 2011/0298169 | A1 * | 12/2011 | Nguyen | A61B 1/125 269/86 |
| 2012/0088973 | A1 * | 4/2012 | Morimoto | A61B 1/00068 600/156 |
| 2012/0088975 | A1 * | 4/2012 | Morimoto | A61B 1/00068 600/159 |
| 2016/0302646 | A1 * | 10/2016 | Hamazaki | A61B 1/00 |
| 2018/0361034 | A1 * | 12/2018 | Tobien | F16K 31/5245 |
| 2019/0125167 | A1 * | 5/2019 | Taniguchi | A61B 1/015 |
| 2019/0350441 | A1 * | 11/2019 | Saiga | A61B 1/00068 |
| 2019/0350444 | A1 * | 11/2019 | Saiga | A61B 1/00068 |
| 2019/0350445 | A1 * | 11/2019 | Saiga | G02B 23/2476 |
| 2019/0350446 | A1 * | 11/2019 | Saiga | A61B 1/00068 |
| 2020/0016637 | A1 * | 1/2020 | Still | A61B 1/125 |
| 2020/0187756 | A1 * | 6/2020 | Maurice | A61B 1/00068 |
| 2020/0355281 | A1 * | 11/2020 | Harris | A61B 1/126 |
| 2020/0375434 | A1 * | 12/2020 | Scutti | A61B 1/00137 |
| 2020/0386330 | A1 * | 12/2020 | Stanton | F16K 31/44 |
| 2021/0007586 | A1 * | 1/2021 | Gavalis | A61B 1/00068 |
| 2021/0076914 | A1 * | 3/2021 | Arai | A61B 1/00119 |

FOREIGN PATENT DOCUMENTS

| | | |
|---|---|---|
| JP | 2000217777 A | 8/2000 |
| JP | 2007111266 A | 5/2007 |
| WO | 2019225562 A1 | 11/2019 |

OTHER PUBLICATIONS

International Search Report and Written Opinion for the International Patent Application No. PCT/US2021/023479, dated Jul. 9, 2021, 12 pages.

International Search Report and Written Opinion for the International Patent Application No. PCT/US2021/023482, dated Jul. 9, 2021, 12 pages.

International Search Report and Written Opinion for the International Patent Application No. PCT/US2021/023484, dated Jul. 9, 2021, 12 pages.

* cited by examiner

100

SUCTION VALVE ASSEMBLY 102

SUCTION VALVE WELL 104

SUCTION CHANNEL 106

WORKING CHANNEL 108

BALLOON CHANNEL 114

ATMOSPHERIC CHANNEL 116

SUCTION VALVE SET 118

WORKING CHANNEL VALVE 120

BALLOON VALVE 122

ATMOSPHERIC VALVE 124

VALVE INTERFACE MECHANISM 126

BIASING MEMBER SET 128

USER INTERFACE MECHANISM 130

AIR/WATER (AW) VALVE ASSEMBLY 202

AW VALVE SET 204

| AIR INPUT CHANNEL 206 | WATER INPUT CHANNEL 208 | AIR OUTPUT CHANNEL 210 |
| --- | --- | --- |
| WATER OUTPUT CHANNEL 212 | BALLOON CHANNEL 214 | ATMOSPHERIC CHANNEL 216 |

AW VALVE SET 218

| PRIMARY CONTROL VALVE 220 | AIR INPUT VALVE 222 | ATMOSPHERIC VALVE 224 |
| --- | --- | --- |

VALVE INTERFACE MECHANISM 226

| BIASING MEMBER SET 228 | USER INTERFACE MECHANISM 230 |
| --- | --- |

FIG. 2

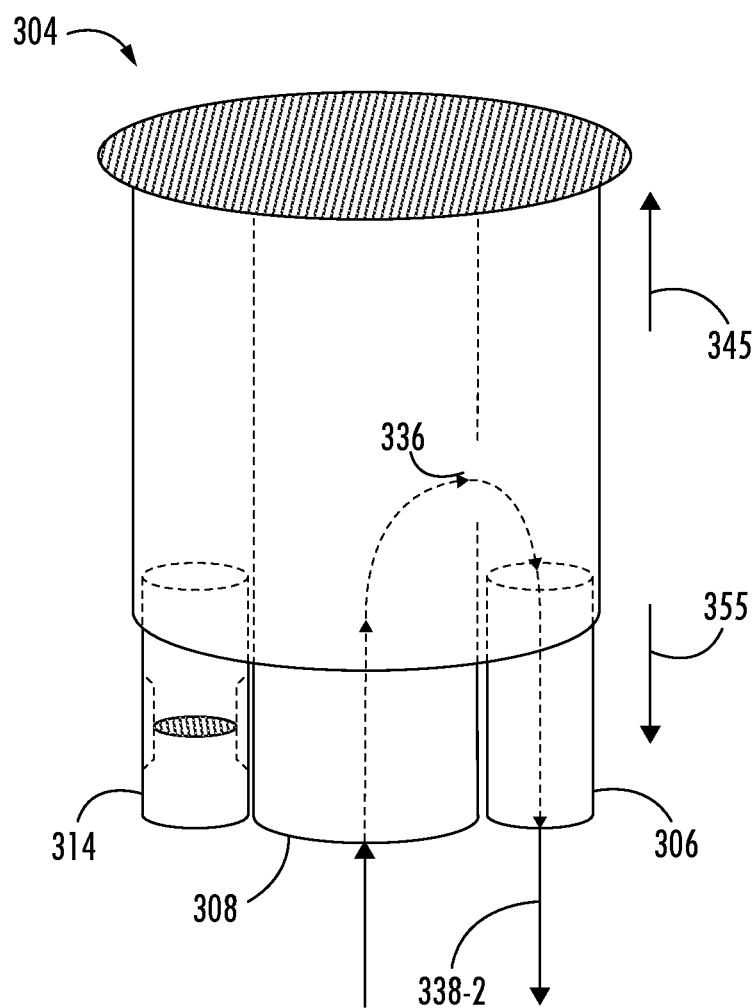

600A

BALLOON VALVE OPEN STATE 615-1

1100A

AIR INPUT VALVE OPEN STATE 1115-1

*1300B*

1400

*1500A*

*1500B*

*1500C*

*1600*

1700A

1700D

1700C

1700B

DEVICES, SYSTEMS, AND METHODS FOR FLUID CONTROL IN ENDOSCOPE SYSTEMS

PRIORITY

The present application claims the benefit of priority under 35 U.S.C. § 119 to U.S. Provisional Application Ser. Nos. 62/994,008, 62/994,015, 62/994,018, 62/994,019, 62/994,021, and 62/994,024, each filed Mar. 24, 2020, the disclosures of which are incorporated herein by reference in their entirety.

FIELD

The present disclosure relates generally to the field of medical devices. In particular, the present disclosure relates to devices, systems, and methods to control flow through a valve well for an endoscope.

BACKGROUND

An endoscopy procedure is used in medicine to access the interior of a body for diagnostic and/or therapeutic procedures. Oftentimes, the endoscopy procedure uses an endoscope to examine or manipulate the interior of a hollow organ or cavity of the body. Unlike many other medical imaging techniques, endoscopes are inserted directly into the organ. Typically, an endoscope includes one or more channels for the flow of one or more fluids therethrough. For example, one or more of suction, air, and water may flow through an endoscope. A valve assembly may be configured and used in various fashion to control the flow of the one or more fluids through the endoscope. In the case of an echoendoscope or ultrasound endoscope, control of fluids may also be used to inflate and deflate a balloon at the end of an endoscope.

It is with these considerations in mind that a variety of advantageous outcomes may be realized by the devices, systems and methods of the present disclosure.

SUMMARY

In one aspect, the present disclosure relates to a medical device, comprising a valve set and a valve interface mechanism. The valve set may include a primary control valve, an air input valve, and an atmospheric valve. The primary control valve may comprise a valve body with an outer surface and one or more channels configured to control flow between a water input channel, a water output channel, and a balloon channel of a valve well. The air input valve may be configured to control flow through an air input channel of the valve well. The atmospheric valve may be configured to control flow through an atmospheric channel. The valve interface mechanism may be operable between a first state, a second state, a third state, and a fourth state. The first state may comprise the valve set configured to place the air input channel in fluid communication with the atmospheric channel, the second state may comprise the valve set configured to place the air input channel in fluid communication with the air output channel, the third state may comprise the valve set configured to place the water input channel in fluid communication with the water output channel, and the fourth state may comprise the valve set configured to place the water input channel in fluid communication with the balloon channel. In some embodiments, the valve interface mechanism, in the first state, may be configured to position the outer surface of the valve body to block flow through the balloon channel, the water input channel, and the water output channel. In various embodiments, the valve interface mechanism, in the second state, may be configured to position the outer surface of the valve body to block flow through the balloon channel, the water input channel, and the water output channel. In several embodiments, the valve interface mechanism, in the third state, may be configured to position a first portion of the one or more channels in fluid communication with the water input channel of the valve well and a second portion of the one or more channels in fluid communication with the water output channel. In several such embodiments, the valve interface mechanism, in the third state, may be configured to position the outer surface of the valve body to block flow through the balloon channel. In one or more embodiments, the valve interface mechanism, in the fourth state, may be configured to position a first portion of the one or more channels in fluid communication with the water input channel of the valve well and a second portion of the one or more channels in fluid communication with the balloon channel. In one or more such embodiments, the valve interface mechanism, in the fourth state, may be configured to position the outer surface of the valve body to block flow through the water output channel. In some embodiments, the valve interface mechanism, in the second state, may be configured to position the outer surface of the valve body to block flow through an air output channel of the valve body. In many embodiments, the valve interface mechanism, in the third state, may be configured to position a first portion of the one or more channels in fluid communication with the air input channel of the valve well and a second portion of the one or more channels in fluid communication with the air output channel of the valve well. In various embodiments, the valve interface mechanism, in the fourth state, may be configured to position the outer surface of the valve body to block flow through an air output channel of the valve body. In several embodiments, the one or more channels comprising one or more manifold channels through the valve body and the outer surface of the valve body may comprise one or more manifold ports, wherein the one or more manifold ports are in fluid communication via the one or more manifold channels. In some embodiments, the one or more channels may be disposed on the outer surface of the valve body. In various embodiments, the valve interface mechanism may be configured to vertically displace the valve body to transition between one or more of the first state and the second state, the second state and the third state, and third state and the fourth state. In many embodiments, the valve interface mechanism may be configured to rotate the valve body to transition between one or more of the first state and the second state, the second state and the third state, and the third state and the fourth state. In several embodiments, the outer surface of the valve body may comprise one or more seals or one or more grooves configured to receive one or more seals.

In another aspect, the present disclosure relates to a medical device comprising a suction valve set and a valve interface mechanism. The suction valve set may include a working channel valve configured to control flow through a working channel of a valve well, a balloon channel of the valve well, and an atmospheric channel. The working channel valve may comprise a valve body with an outer surface and one or more channels. The valve interface mechanism may operable between a first state, a second state, and a third state, the first state comprising the suction valve set configured to place a suction channel of the valve well in fluid communication with the atmospheric channel, the second state comprising the suction valve set configured to place the suction channel in fluid communication with the working channel, and the third state comprising the suction valve set configured to place the suction channel in fluid communication with the balloon channel. In some embodiments, the valve interface mechanism, in the first state, may be configured to position a first portion of the one or more channels in fluid communication with the atmospheric channel and a second portion of the one or more channels in fluid communication with the suction channel. In various embodiments, the valve interface mechanism, in the second state, may be configured to position a first portion of the one or more channels in fluid communication with the suction channel and a second portion of the one or more channels in fluid communication with the working channel. In various such embodiments, the valve interface mechanism, in the second state, may be configured to position the outer surface of the valve body to block flow through the atmospheric channel. In one or more embodiments, the valve interface mechanism, in the third state, may be configured to position the outer surface of the valve body to block flow through the working channel. In one or more such embodiments, the valve interface mechanism, in the second state, may be configured to position the outer surface of the valve body to block flow through the atmospheric channel.

In yet another aspect, the present disclosure relates to a method. The method may include placing a suction channel of a valve well in fluid communication with an atmospheric channel of the valve well based on operation of a user interface mechanism to a first state. The method may include, placing the suction channel of the valve well in fluid communication with a working channel of the valve well based on operation of the user interface mechanism to a second state. The method may include placing the suction channel of the valve well in fluid communication with a balloon channel of the valve well based on operation of the user interface mechanism to a third state. In some embodiments, the method may include rotating an interface member in a first direction to operate the user interface mechanism to the second state and rotating the interface member in a second direction to operate the user interface mechanism to the third state. In many embodiments, the method may include rotating the interface member adjust one or more valves in a suction valve set via a cam. In several embodiments, the method may include operating one or more of a lever, a rocker switch, and an interface member to adjust between one or more of the first state, the second state, and the third state.

In still another aspect, the present disclosure relates to a method. The method may include configuring a valve set to place an air input channel of a valve well in fluid communication with an atmospheric channel based on operation of a valve interface mechanism to a first state, the valve set comprising a primary control valve comprising a valve body with an outer surface and one or more channels. The method may include configuring the valve set to place the air input channel in fluid communication with an air output channel of the valve well based on operation of the valve interface mechanism to a second state. The method may include configuring the primary control valve of the valve set to place the water input channel in fluid communication with a water output channel of the valve well based on operation of the valve interface mechanism to a third state. The method may include configuring the primary control valve of the valve set to place the water input channel in fluid communication with the balloon channel of the valve well based on operation of the valve interface mechanism to a fourth state. In some embodiments, the method may include configuring the valve interface mechanism to vertically displace the valve body to transition between one or more of the first state and the second state, the second state and the third state, and the third state and the fourth state. In various embodiments, the method may include configuring the valve interface mechanism to rotate the valve body to transition between one or more of the first state and the second state, the second state and the third state, and the third state and the fourth state.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 includes a block diagram of an exemplary suction valve assembly, according to one or more embodiments described herein.

FIG. 2 includes a block diagram of an exemplary air/water (AW) valve assembly, according to one or more embodiments described herein.

FIGS. 3A-3D illustrate various aspects of an exemplary suction valve well, according to one or more embodiments described herein.

DETAILED DESCRIPTION

Figure 3A:
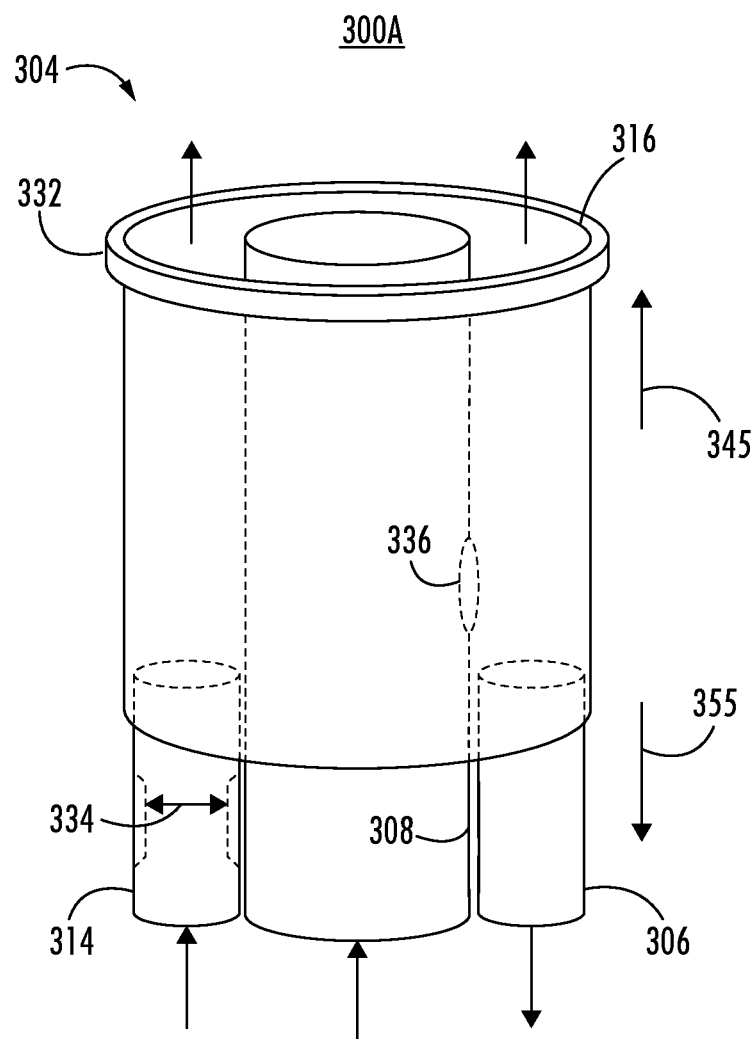

Various embodiments are generally directed to devices, systems, and methods for controlling the flow of fluids in endoscopic systems, such as endoscopic ultrasound (EUS)

enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve control motions. In one or more embodiments, the valve sets and/or valve interface mechanisms may be disposable. These and other embodiments are described and claimed.

Some challenges when controlling the flow of fluids through endoscopes include unreliable valves prone to failure. For example, many valves and valve interface mechanisms are fragile and likely to leak. These issues can be compounded when the components are designed, constructed, and/or assembled economically to facilitate disposal after a single use. Alternatively, these issues can be compounded when reusable components are worn down from multiple use/cleaning cycles. Adding further complexity, user interface mechanisms may be confusing to operate and require a steep learning curve. For instance, delicate and nonintuitive movements may be required to accurately control fluid flows. Further, little or no feedback may be provided to indicate how a set of valves is arranged. For example, an operator may not be able to easily discern via a user interface mechanism whether the set of valves is arranged to provide suction to a working channel or provide suction to a balloon channel. These and other factors may result in devices, systems, and methods for controlling the flow of fluids through endoscopes that are difficult to use, inaccurate, inefficient, and unreliable, resulting in limited applicability and/or uncertain outcomes. Such limitations can drastically reduce the dependability, ergonomics, and intuitiveness of flow control in endoscopes and procedures performed therewith, contributing to reduced usability, adverse outcomes, excess fatigue, and lost revenues.

Various embodiments described herein include one or more components of a valve assembly, such as valves and/or valve interface mechanisms, that provide reliable and intuitive control of fluid flow through endoscopes. In several embodiments, the components may provide reliable operation while providing sufficient value to be disposable (e.g., single-use). In many embodiments, the components may provide accurate and intuitive interfaces to improve operator experience. For example, embodiments may utilize one or more of up-and-down, forward-and-back, side-to-side, and rotational interfaces to provide ergonomic and intuitive control of fluid flows through endoscopes. Some such embodiments may include one or more interface members, such as push/pull switches, bellows, rotational switches, knobs, buttons, and toggle switches. In many embodiments, one or more of the components may provide/enable tactile feedback. For example, one or more components of the valve interface mechanism may provide tactile or haptic feedback to indicate how a set of valves is arranged (e.g., arranged to permit/block flows between various channels). In some examples, the force to operate a user interface mechanism may vary to indicate transitions between valve states. In various embodiments, tactile feedback may be produced as a result of different components of a valve assembly coming into contact, such as due to received input.

In various embodiments, one or more of the components may be designed to simplify manufacturability. For instance, the location of one or more biasing members may simplify component assembly. In these and other ways, components/techniques described here may improve operator experience, decrease learning curves, improve reliability, and/or decrease manufacturing complexity via realization of more efficient and valuable devices, systems, and methods for controlling the flow of fluids in endoscopic systems. In many embodiments, one or more of the advantageous features may result in several technical effects and advantages over conventional technology, including increased capabilities and improved adaptability.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to specific medical devices and systems (e.g., an endoscope), it should be appreciated that such medical devices and systems may be used in a variety of medical procedures which require navigating one or more accessory tools through ductal, luminal, or vascular anatomies, including, for example, interventional radiology procedures, balloon angioplasty procedures, thrombolysis procedures, angiography procedures, Endoscopic Retrograde Cholangio-Pancreatography (ERCP) procedures, and the like. The disclosed medical devices and systems may be inserted via different access points and approaches, e.g., percutaneously, endoscopically, laparoscopically or some combination thereof.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional/operator when introducing a device into a patient, while the term "proximal" refers to the end closest to the medical professional when introducing a device into a patient.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIGS. 1 and 2 illustrate block diagrams of exemplary valve assemblies in environments 100, 200, according to one or more embodiments described herein. In some embodiments, one or more components of environment 100 and/or environment 200 may be the same or similar to one or more other components described herein. Environment 100 may include a suction valve assembly 102 with a suction valve well 104, a suction valve set 118, and a valve interface mechanism 126. Environment 200 may include an air/water (AW) valve assembly 202 with an AW valve well 204, an AW valve set 218, and a valve interface mechanism 226. In one or more embodiments described herein, various components of suction valve assembly 102 and/or AW valve assembly 202 may interoperate to provide reliable and intuitive control of fluid flow through endoscopic systems. For example, one or more components of valve sets 118, 218 and valve interface mechanisms 126, 226 may reliable and intuitive control of fluid flow through suction valve well 104 or AW valve well 204. In many embodiments, components of a valve assembly may be classified as, belong to, include, implement, and/or interoperate with one or more of a valve well, a valve set, and a valve interface mechanism. For instance, a valve interface mechanism may include one or more portions of a valve. Embodiments are not limited in this context.

In environment 100, the suction valve well 104 may include suction channel 106, working channel 108, balloon channel 114, and atmospheric channel 116; the suction valve set 118 may include working channel valve 120, balloon valve 122, and atmospheric valve 124; and the valve interface mechanism 126 may include biasing member set 128 and user interface mechanism 130. In various embodiments, the channels of the suction well 104 may be connected to other components in an endoscopic system, such as via tubing or piping. In one or more embodiments described herein, the suction channel 106 may be connected to a suction source, the working channel 108 may be connected to a working channel of an endoscopic device (e.g., endoscope or component disposed therethrough), the balloon channel 114 may be connected to a balloon of an endoscopic device. In several embodiments, suction valve set 118 and valve interface mechanism 126 may control the flow of suction (e.g., induced by negative pressure relative to atmospheric pressure) through suction valve well 104. In several such embodiments, the flow of suction may be controlled to the suction channel 106 from one of the working channel 108, the balloon channel 114, and the atmospheric channel 116.

In environment 200, the AW valve well 204 may include air input channel 206, water input channel 208, air output channel 210, water output channel 212, balloon channel 214, and atmospheric channel 216; the AW valve set 218 may include primary control valve 220, air input valve 222, and atmospheric valve 224; and the valve interface mechanism 226 may include biasing member set 228 and user interface mechanism 230. In various embodiments, the channels of the AW well 204 may be connected to other components in an endoscopic system, such as via tubing or piping. In one or more embodiments described herein, the air input channel 206 may be connected to a pressurized air source, the water input channel 208 may be connected to a water source, the air output channel 210 may be connected to an air channel of an endoscopic device (e.g., endoscope or component disposed therethrough), the water output channel 212 may be connected to a water channel of an endoscopic device, and the balloon channel 214 may be connected to a balloon of an endoscopic device. In several embodiments, AW valve set 218 and valve interface mechanism 226 may control the flow of air and water through AW valve well 204. In several such embodiments, the flow of air may be controlled from air input channel 206 to one of the air output channel 210, the atmospheric channel 216, or blocked and/or the flow of water may be controlled from water input channel 208 to one of water output channel 212 and balloon channel 214.

In many embodiments, suction valve assembly 102 and/or AW valve assembly 202 may be used in conjunction with an endoscopic system, such as an EUS system. In various embodiments, reference to a balloon may refer to a balloon in the EUS system that can be inflated/deflated to facilitate capturing of ultrasound images. For example, valve interface mechanism 126 may receive input to control the flow through suction valve well 104 to deflate the balloon by arranging the suction valve set 118 to place the suction channel 106 in fluid communication with the balloon channel 114. In another example, valve interface mechanism 226 may receive input to control the flow of water through AW valve well to inflate the balloon by arranging the AW valve set 218 to place the water input channel 208 in fluid communication with balloon channel 214.

More generally, in several embodiments, each channel in a valve well may refer to a flow path comprising an input/output of a fluid from/to a corresponding entity. For example, suction channel 106 may refer to a flow path comprising an input from a suction source. In another example, an atmospheric channel may refer to a flow path comprising an output to the atmosphere. These and other aspects of the present disclosure will be described in more detail below, such as with respect to FIGS. 3A-4E. In various embodiments, each valve in a valve set may refer to a component that physically controls flow through or between one or more channels. For instance, when closed, the atmospheric valve 124 may block the flow of air out of the atmospheric channel 116. In another instance, in a first position, or first state, the primary control valve 220 may place the water input channel 208 in fluid communication with the water output channel 212, and in a second position, the primary control valve 220 may place the water input channel 208 in fluid communication with the balloon channel 214. These and other aspects of the present disclosure will be described in more detail below, such as with respect to FIGS. 5-12C.

In various embodiments, the valve interface mechanisms may include one or more components to enable control over the arrangement of valves in a valve set. In such embodiments, biasing member sets may include one or more, torsional springs, lever springs, coil spring, baffles, dampers, clips, and the like that provide a force to bias one or more components in a specific direction or position. For example, the biasing member set 228 may cause air to flow out the atmospheric channel when no input is being received. In an additional, or alternative example, the biasing member set 128 may provide differing resistance to operation of the user interface mechanism 130 between different states, such as to provide tactile indications of the state. In various embodiments, each of the user interface mechanisms 130, 230 may include one or more of an interface, an interface member, a user interface, a housing, a linkage, a knob, a levers, a rocker switch, a push/pull switch, a knob, a button, a diaphragm switch, a toggle switch, and the like. In some embodiments, an interface, an interface member, and/or a user interface may be the same or similar.

In several embodiments, user interface mechanisms may include one or more components to receive input and/or implement valve arrangements. For example, user interface mechanism 130 may include a user interface comprising a lever and one or more linkages to translate motion of the lever into appropriate motion of one or more valves to achieve a desired flow. In various embodiments, user interface mechanisms may include one or more biasing members and/or biasing members may include one or more user interface mechanisms. It will be appreciated that one or more components described herein in the context of a suction valve assembly may be utilized in or adapted for use in an AW valve assembly, and vice versa without departing from the scope of this disclosure. For example, a rotational user interface mechanism described with respect to a suction valve interface mechanism may be utilized in or adapted for use in an AW valve interface mechanism. These and other aspects of the present disclosure will be described in more detail below.

FIGS. 3A-4E illustrate various aspects of exemplary valve wells block diagrams of exemplary valve assemblies in environments 300A-D, 400A-E, according to one or more embodiments described herein. In some embodiments, one or more components of FIGS. 3A-4E may be the same or similar to one or more other components described herein. Environments 300A-D illustrate a suction valve well 304 comprising a suction channel 306, a working channel 308, a balloon channel 314 and an atmospheric channel 315. Environments 400A-E illustrate an AW valve well 404 with an air input channel 406, a water input channel 408, an air output channel 210, a water output channel 212, a balloon channel 214, and an atmospheric channel 216. In one or more embodiments described herein, fluid may flow through the valve wells based on the arrangement of one or more valves as positioned by one or more valve interface mechanisms. Embodiments are not limited in this context.

Referring to FIG. 3A, environment 300A illustrates various components of suction valve well 304. The suction valve well 304 may include a top 345 and a bottom 335. The suction channel 306, working channel 308, and balloon channel 314 may comprise respective entrances/exits towards the bottom 355 while the atmospheric channel 316 may comprise an entrance towards the top 345. In the illustrated embodiment, the balloon channel 314 includes a necking portion 334, the working channel 308 includes a well radial hole 336, and the atmospheric channel 316 includes a lip 332. In one or more embodiments, the necking portion 334 may enable a valve to prevent fluid flow through the balloon channel 314, such as by blocking the necking portion 334. In various embodiments, the well radial hole 336 may enable the working channel 308 to be placed in fluid communication with the suction channel 306. In several embodiments, the lip 332 may enable one or more suction valve sets and/or valve interface mechanisms to couple to the suction valve well 304. In many embodiments, valves and/or valve interface mechanisms may be inserted through atmospheric channel 316 for assembly of a suction valve assembly. It will be appreciated that the orientation and/or arrangement of one or more of the channels and/or flows may be modified in various embodiments without departing from the scope of this disclosure.

Figure 3B:
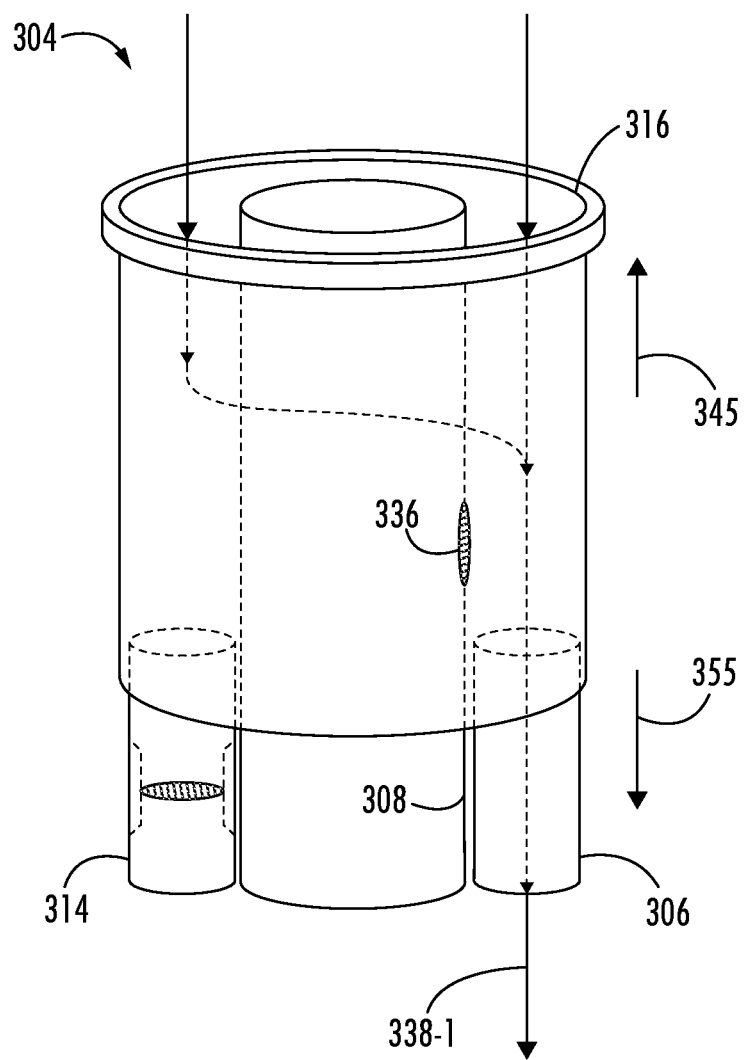

Referring to FIG. 3B, environment 300B illustrates a flow 338-1 through the suction valve well 304 in an atmospheric suction state 305-1. In the atmospheric suction state 305-1, flow 338-1 may enter via the atmospheric channel 316 and exit through the suction channel 306. Further, in some embodiments, flow may be blocked through the balloon channel 314 at the necking portion 334 and flow may be blocked through the working channel 308 at the well radial hole 336. As will be discussed in more detail below, in operation, fluid communication with the atmosphere may be provided through a passage/channel in, or created by, one or more components (e.g., a valve inserted into the atmospheric channel 316). Further, one or more components may be used to seal portions of the atmospheric channel 316 to facilitate blocking of fluid communication with the atmosphere by an atmospheric valve.

Referring to FIG. 3C, environment 300C illustrates a flow 338-2 through the suction valve well 304 in a working channel suction state 305-2. In the working channel suction state 305-2, flow 338-2 may enter via the working channel 308, pass through the well radial hole 336, and exit through the suction channel 306. Further, in many embodiments, flow may be blocked through the balloon channel 314 at the necking portion 334 and flow may be blocked through the atmospheric channel 316.

Figure 3D:
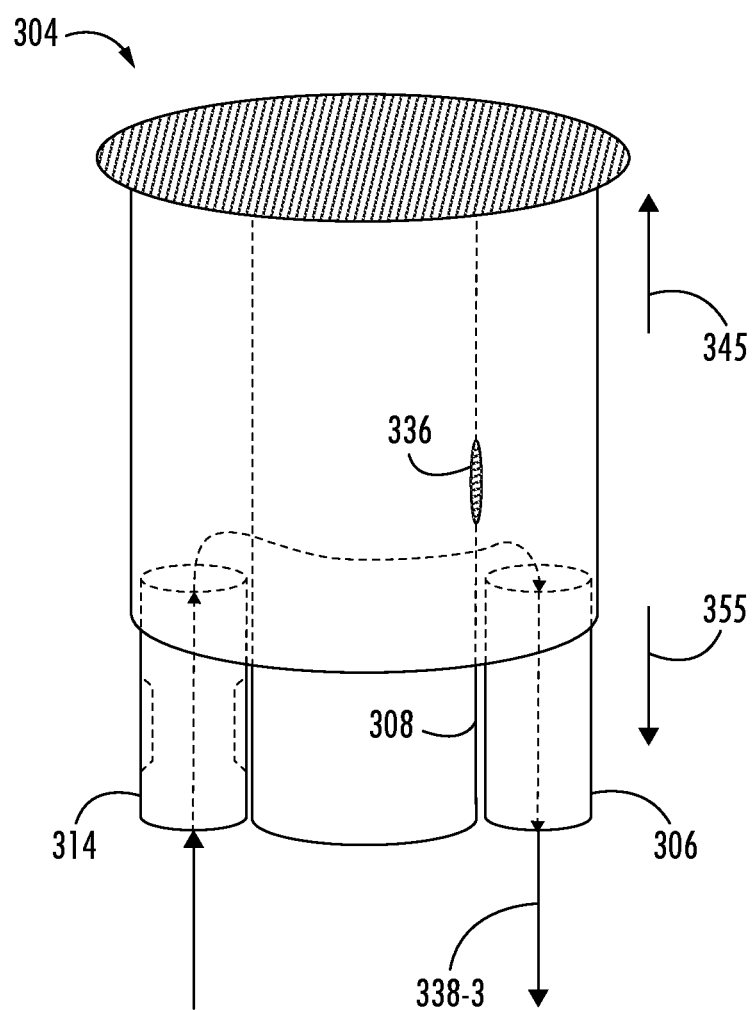

Referring to FIG. 3D, environment 300D illustrates a flow 338-3 through the suction valve well 304 in a balloon channel suction state 305-3. In the balloon channel suction state 305-3, flow 338-3 may enter via the balloon channel 314 and exit through the suction channel 306. Further, in several embodiments, flow may be blocked through the working channel 308 at the well radial hole 336 and may be blocked through the atmospheric channel 316.

Figure 4A:
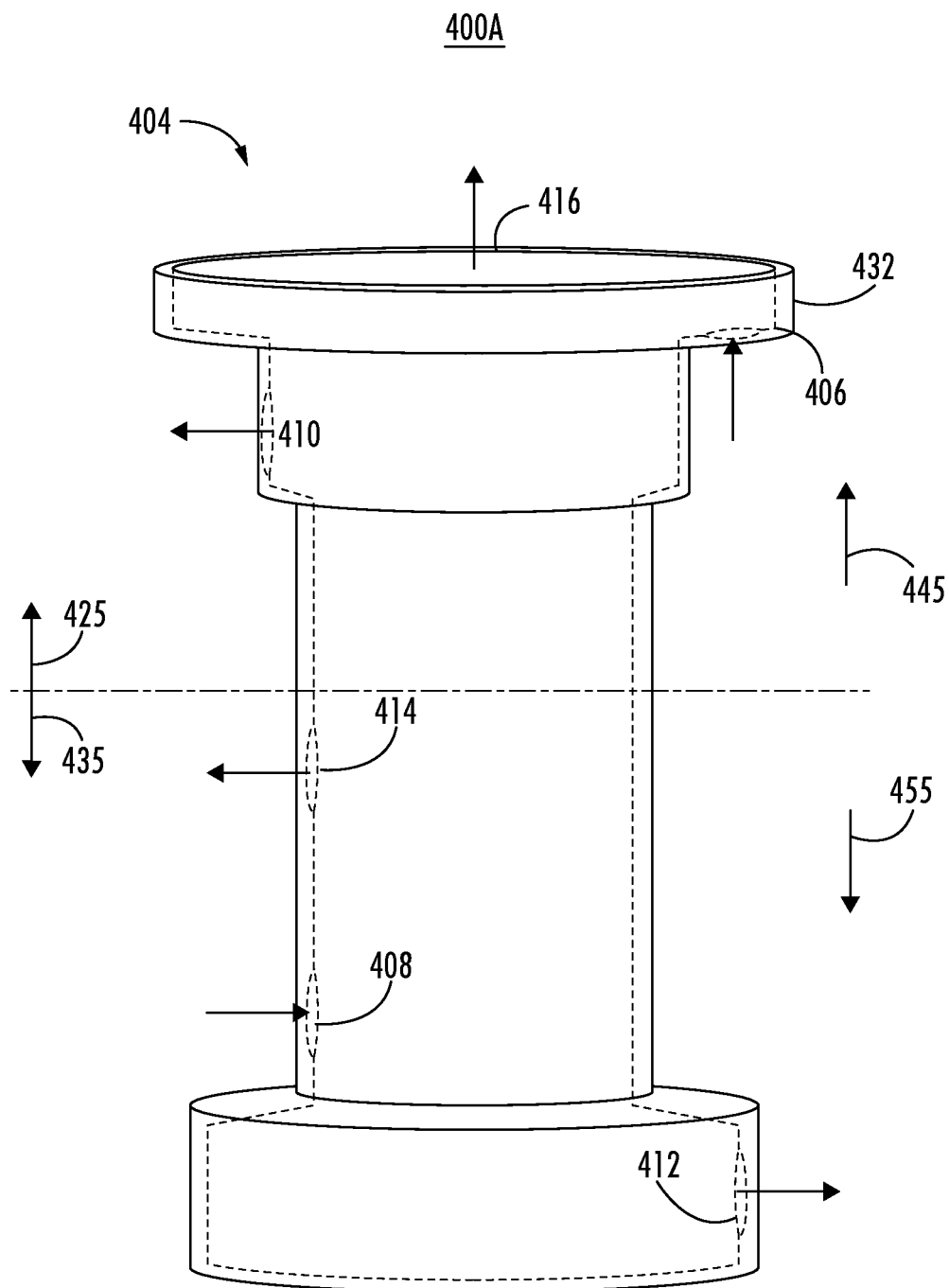
FIGS. 4A-4E illustrate various aspects of an exemplary AW valve well, according to one or more embodiments described herein.

Referring to FIG. 4A, environment 400A illustrates various components of AW valve well 404. The AW valve well 404 may include a top 445 and a bottom 435 and/or an air portion 425 and a water portion 435. The air output channel 410, air input channel 412, and atmospheric channel 416 may be in the air portion 425. The atmospheric channel 416 may comprise a horizontally-oriented exit towards the top 345 and lip 432, the air input channel 412 may comprise a horizontally-oriented entrance towards the top 345, the air output channel 410 may comprise a vertically-oriented exit towards the top. The water input channel 408, water output channel 412, and balloon channel 414 may be in the water portion 435. The balloon channel 414 may comprise a vertically-oriented exit proximate the middle, the water input channel 408 may comprise a vertically-oriented entrance toward the bottom 455, and the water output channel 412 may comprise a vertically-oriented exit toward the bottom 455. In several embodiments, the lip 432 may enable one or more suction valve sets and/or valve interface mechanisms to couple to the AW valve well 404.

In several embodiments, the AW valve well 404 may change diameters one or more times. For example, the diameter changes in conjunction with vertical displacement of a valve may enable flow around the valve and through a channel. In the illustrated embodiment, the AW valve well may have a first diameter comprising the entrance/exits of the air input/atmospheric channels 412, 416, a second diameter comprising the exit of the air output channel 410, a third diameter comprising the entrance/exit of the water input/balloon channels 408, 414, and a fourth diameter comprising the exit of the water output channel 412. It will be appreciated that the orientation, size, and/or arrangement of one or more of the channels and/or flows may be modified in various embodiments without departing from the scope of this disclosure.

Figure 4B:
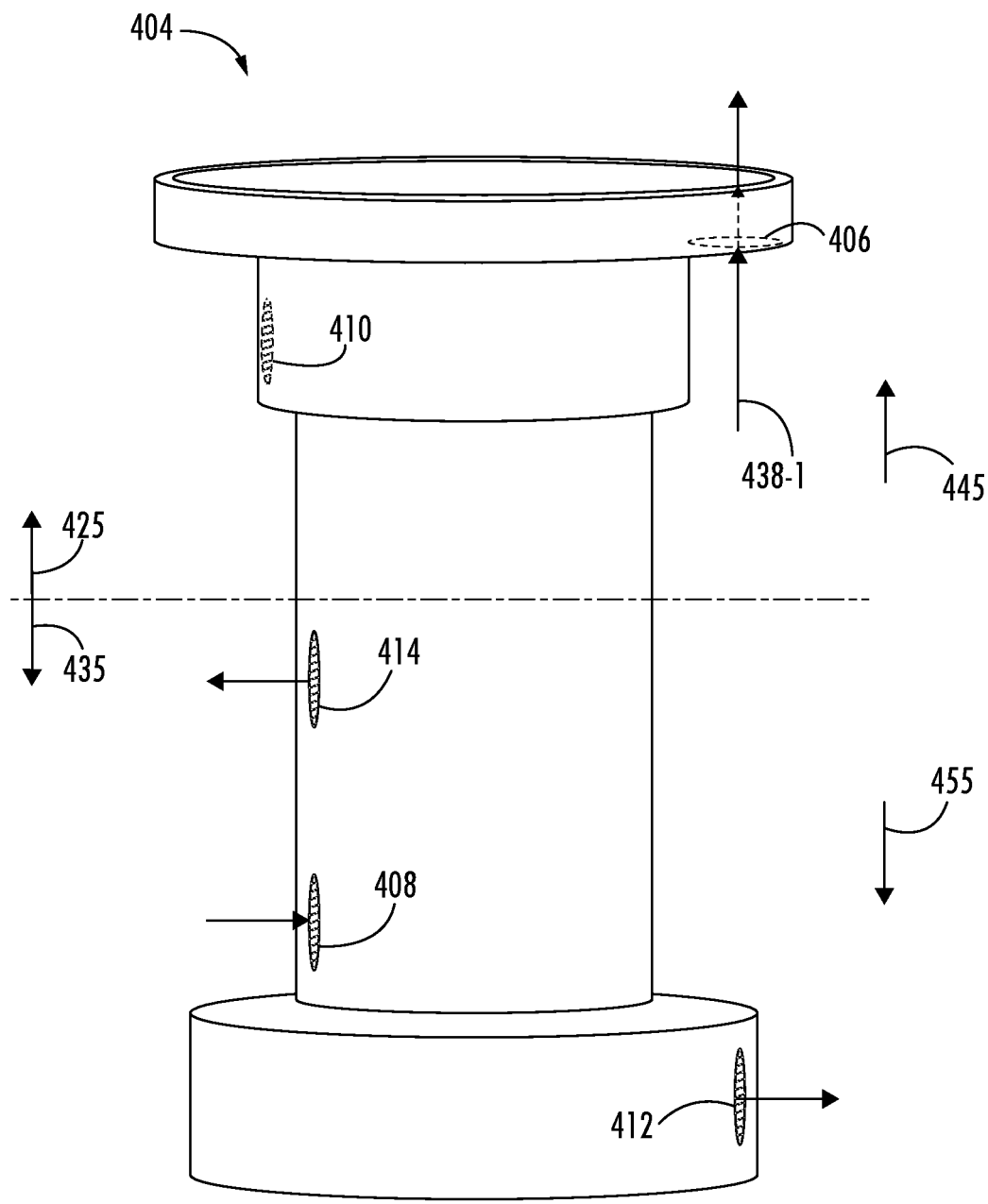

Referring to FIG. 4B, environment 400B illustrates a flow 438-1 through the AW valve well 404 in an air escape state 405-1. In the air escape state 405-1, flow 438-1 may enter via air input channel 406 and exit through the atmospheric channel 416. Further, in some embodiments, flow may be blocked through one or more of balloon channel 414, water input channel 408, and water output channel 412.

Figure 4C:
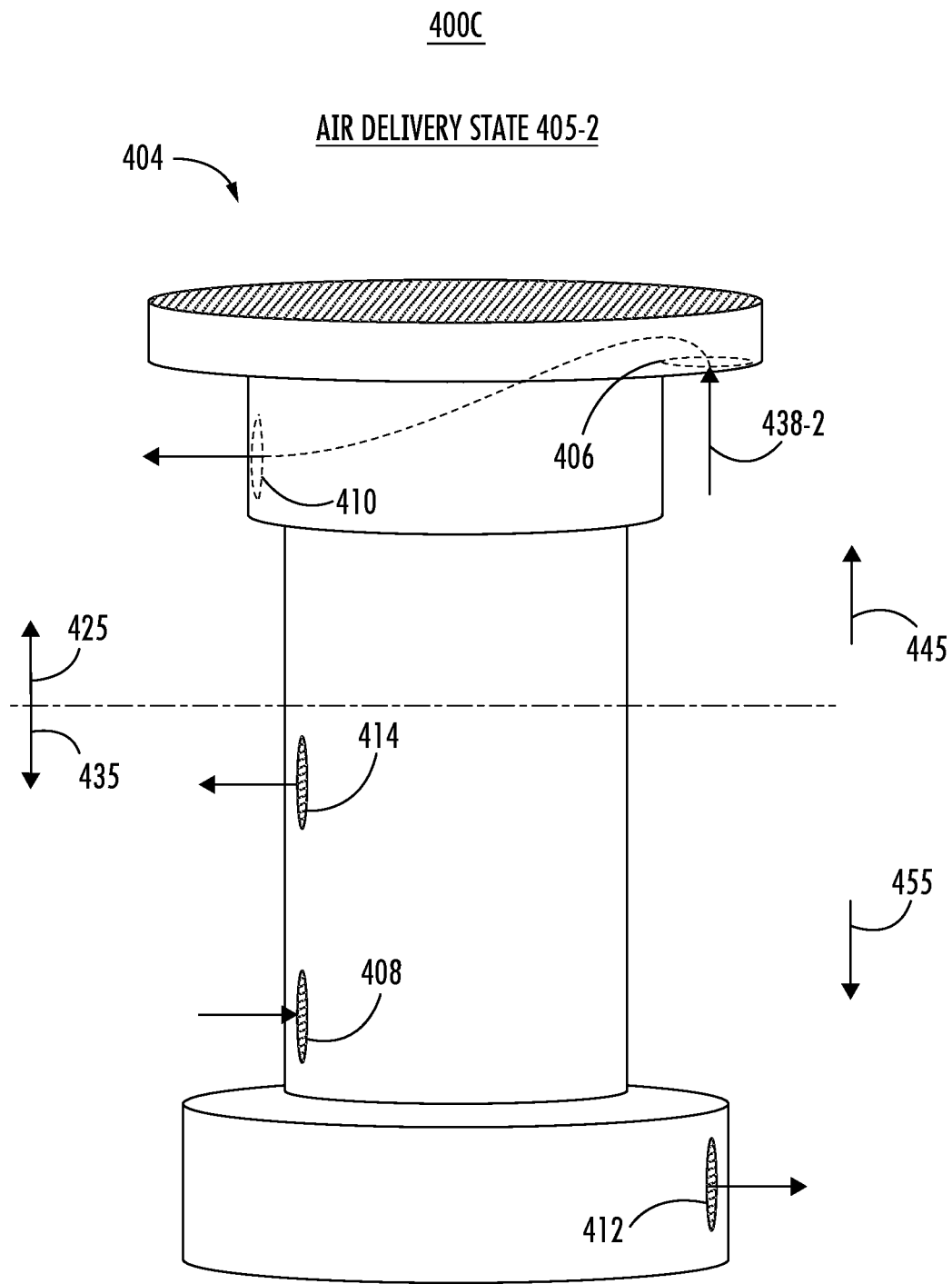

Referring to FIG. 4C, environment 400C illustrates a flow 438-2 through the AW valve well 404 in an air delivery state 405-2. In the air delivery state 405-2, flow 438-2 may enter via the air input channel 406 and exit through the air output channel 410. Further, in various embodiments, flow may be blocked through one or more of atmospheric channel 416, balloon channel 414, water input channel 408, and water output channel 412.

Figure 4D:
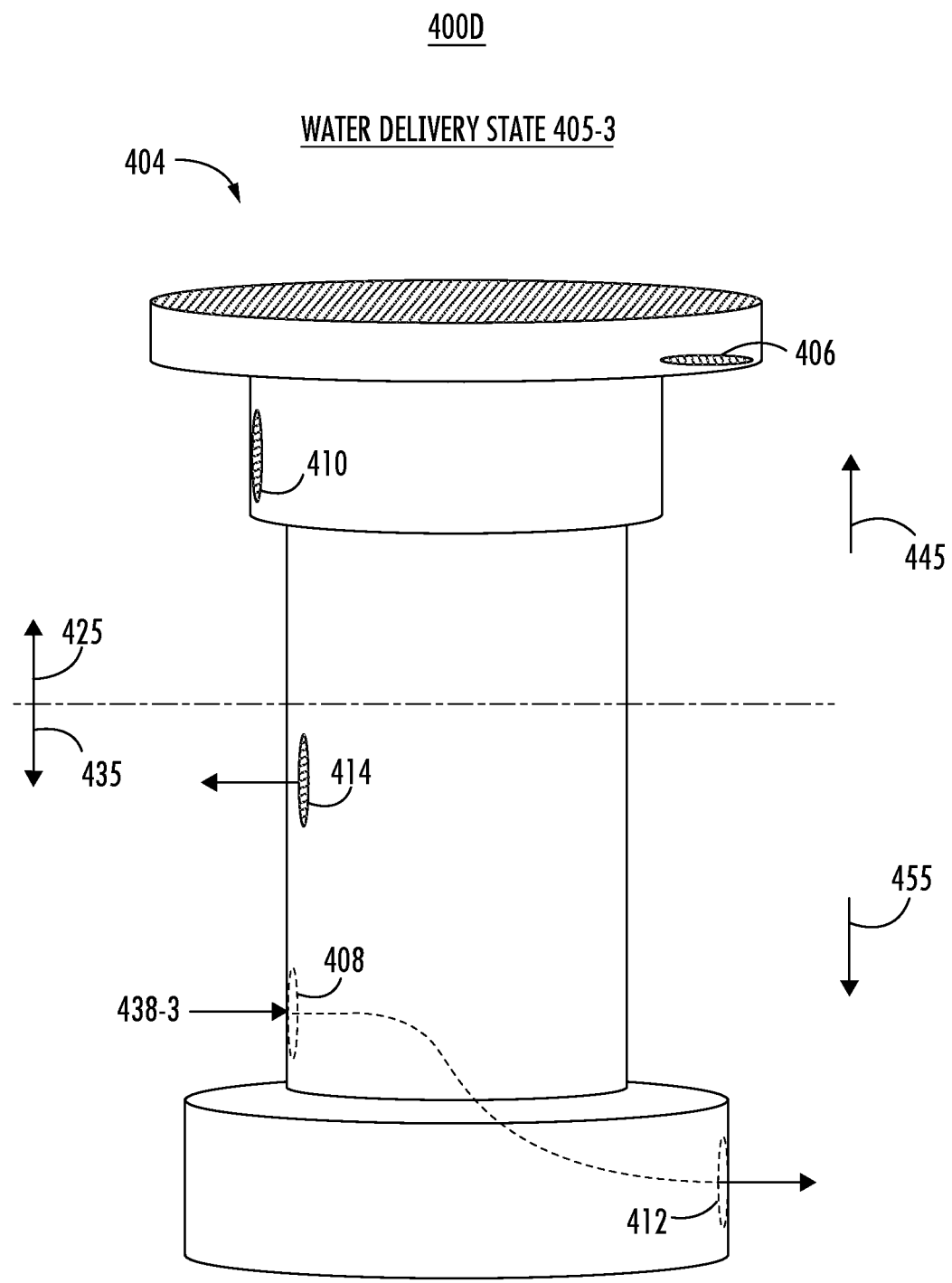

Referring to FIG. 4D, environment 400D illustrates a flow 438-3 through the AW valve well 404 in a water delivery state 405-3. In the water delivery state 405-3, flow 438-3 may enter via water input channel 408 and exit through the water output channel 412. Further, in various embodiments, flow may be blocked through one or more of the balloon channel 414, air output channel 410, air input channel 406, and atmospheric channel 416. In various embodiments, blocking flow at the air input channel 406 may cause pressure to build in a water source feeding the water input channel 408. In various such embodiments, pressure in the water source may cause fluid to flow from the water source to water input channel 408.

Figure 4E:
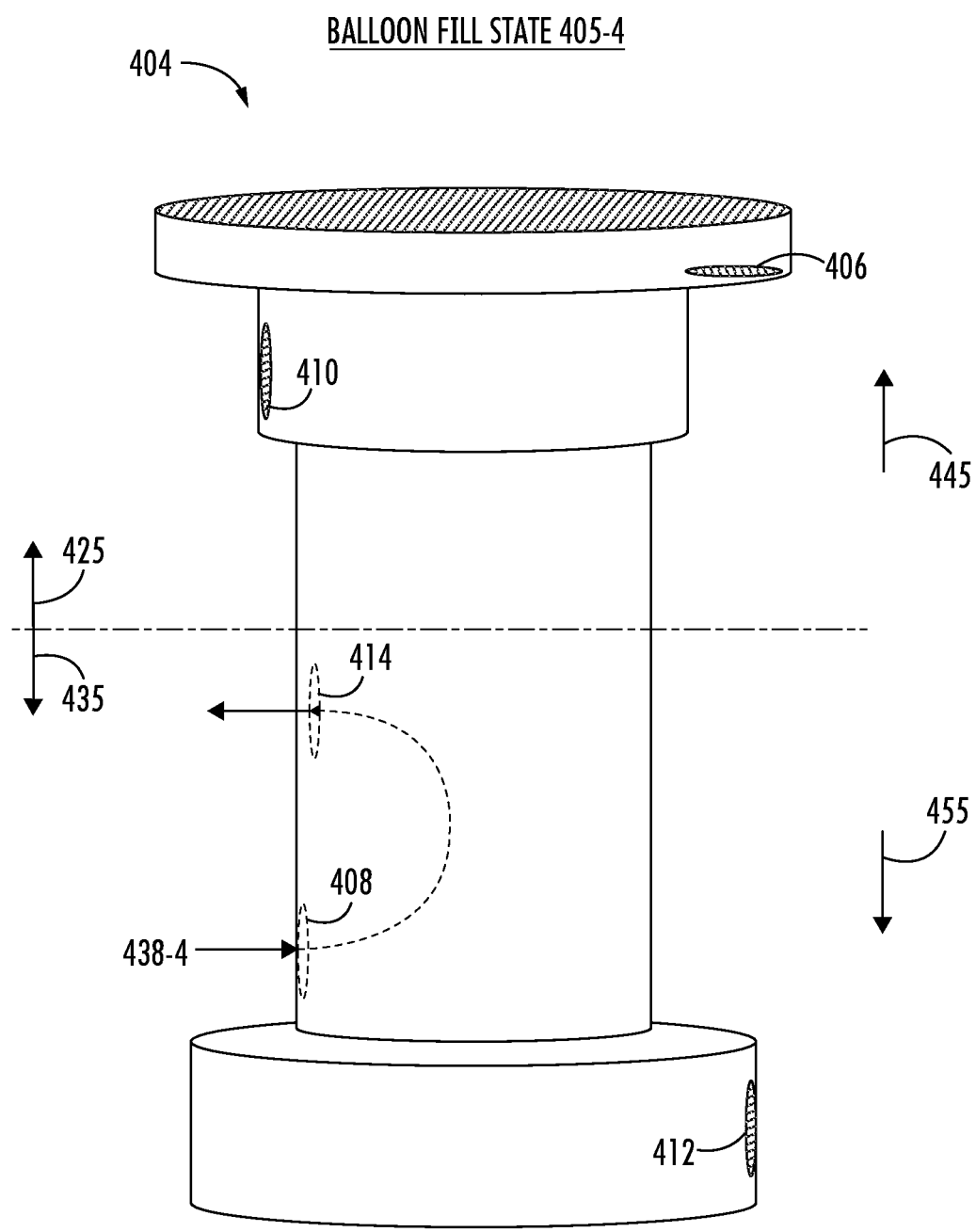

Referring to FIG. 4E, environment 400E illustrates a flow 438-4 through the AW valve well 404 in a balloon fill state 405-4. In the balloon fill state 405-4, flow 438-4 may enter via the water input channel 408 and exit through the balloon channel 414. Further, in many embodiments, flow may be blocked through one or more of the water output channel 412, air output channel 410, air input channel 406, and atmospheric channel 413.

FIGS. 5-12C illustrate various aspects of exemplary valve sets in environments 500, 600A, 600B, 700A, 700B, 800A-C, 900, 1000A, 1000B, 1100A, 1100B, 1200A-C, according to one or more embodiments described herein. In some embodiments, one or more components of FIGS. 5-12C may be the same or similar to one or more other components described herein. Environments 500-800C illustrate various aspects of a suction valve set 518 in conjunction with one or more components of suction valve well 304. Environments 900-1200C illustrate various aspects of an AW valve set 918 in conjunction with one or more components of AW valve well 404. In one or more embodiments described herein, fluid may flow through the valve wells based on the arrangement of one or more valves as positioned by one or more valve interface mechanisms. In many embodiments, one or more valves described herein may include a plurality of components configured to control fluid through a valve well. Embodiments are not limited in this context.

Figure 5:
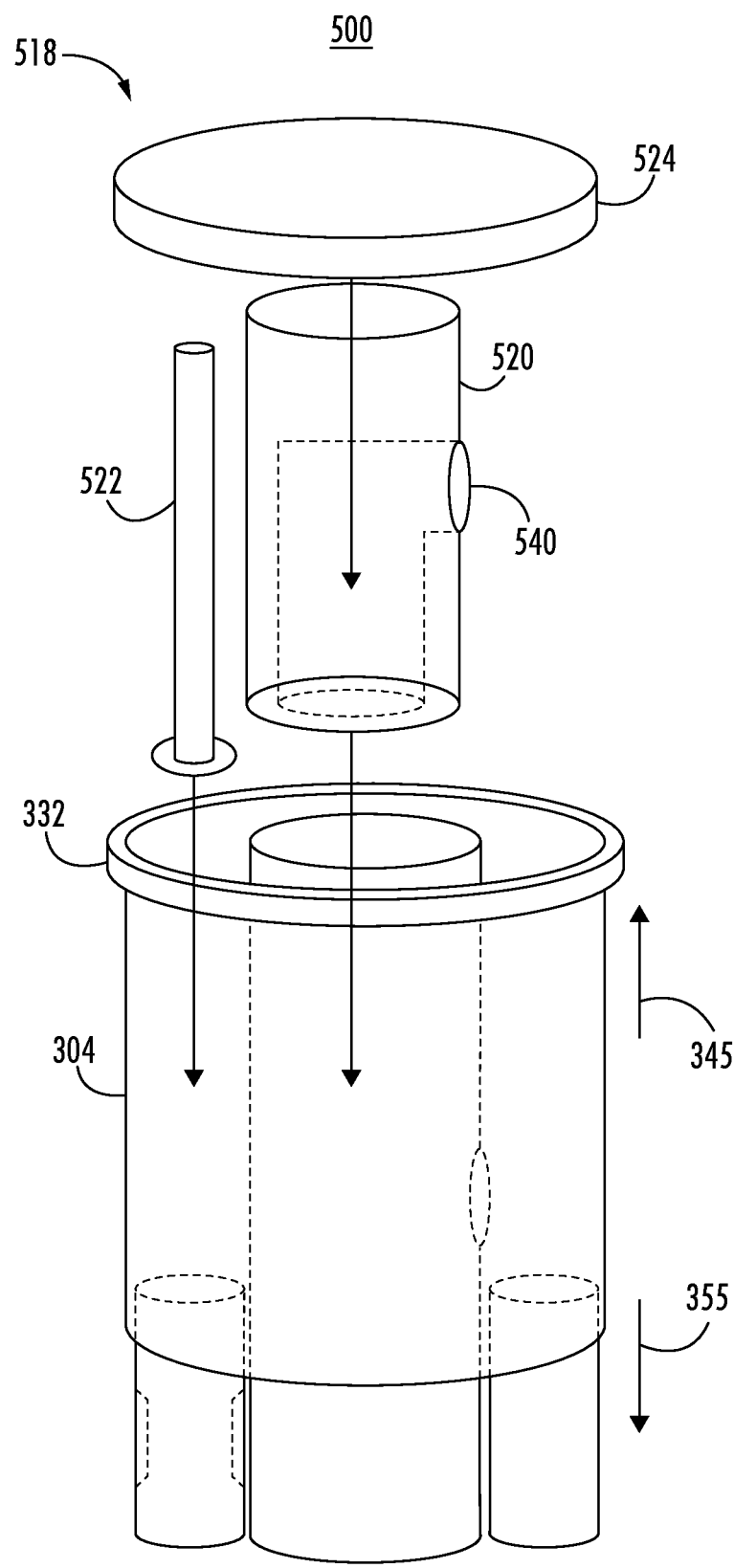
FIG. 5 illustrates an exemplary suction valve set, according to one or more embodiments described herein.

Referring to FIG. 5, environment 500 illustrates suction valve set 518 in conjunction with suction valve well 304. Suction valve set 518 may include working channel valve 520, balloon valve 522, and atmospheric valve 524. The working channel valve 520 may include a working channel valve radial hole 540 that enables fluid to flow into the working channel valve 520 out of the bottom of the working channel valve 520. In several embodiments, the working channel valve 520 may be inserted into the working channel of suction valve well 304 to control flow therethrough. The balloon valve 522 may be inserted into balloon channel of suction valve well 304 to control flow therethrough. The atmospheric valve 524 may be inserted into the atmospheric channel of suction valve well 304 to control flow therethrough. In many embodiments, one or more valves in suction valve set 518 may be integrated with one or more portions of a housing and/or valve interface mechanism corresponding to suction valve well 304.

In one or more embodiments, the atmospheric valve 524 may be configured to control fluid communication with the atmosphere from the interior of the suction valve well 304. In many embodiments, the atmospheric valve 524 may include a hole in a housing. In some embodiments, the atmospheric valve 524 may be operated by covering and/or uncovering the hole, such as with a finger or other mechanism. In several embodiments, the positioning and/or configuration of the valves in suction valve set 518 may be controlled by one or more components of a corresponding valve interface mechanism. For example, depressing a valve interface mechanism to a first stop may simultaneously shut off atmospheric suction via a seal on the underside of a cap and open working channel suction by pushing down the center of the working channel valve 520 to align the working channel valve radial hole 540 and the well radial hole.

Figure 6A:
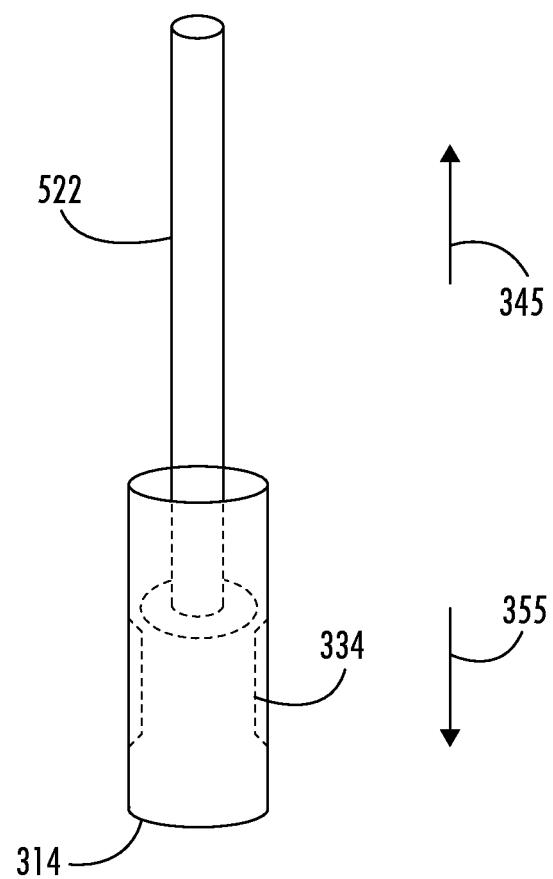
FIGS. 6A-8C illustrate various aspects of exemplary valves in suction valve sets, according to one or more embodiments described herein.
Figure 6B:
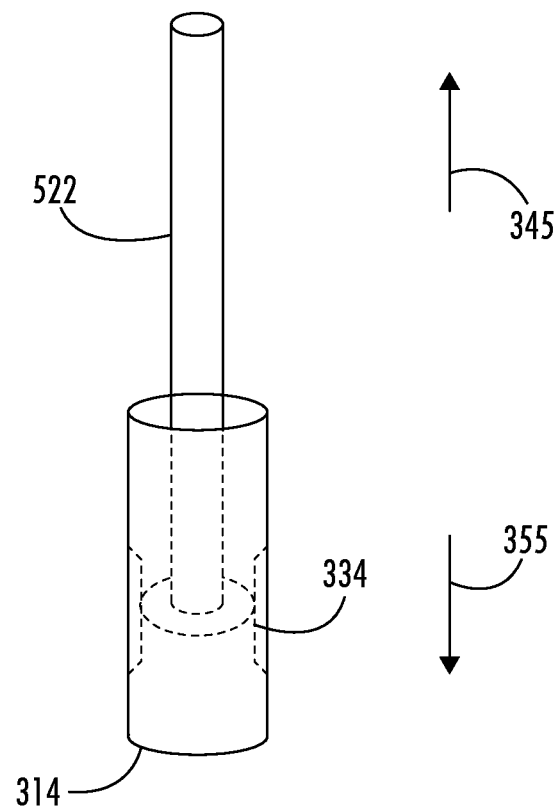

Referring to FIG. 6A, environment 600A illustrates a balloon valve open state 615-1. In the balloon valve open state 615-1, the balloon valve 522 may allow flow through the balloon channel 314 by permitting flow through the necking portion 334 of balloon channel 314. Referring to FIG. 6B, environment 600B illustrates a balloon valve sealed state 615-2. In the balloon valve sealed state 615-2, the balloon valve 522 may prevent flow through balloon channel 314 by blocking flow through the necking portion 334 of balloon channel 314. In additional, or alternative embodiments, the default state of the balloon valve 522 may be the balloon valve sealed state 615-2 and the balloon valve 522 may be depressed toward the bottom 355 and below the necking portion 334 to transition into the balloon valve open state 615-1.

Figure 7A:
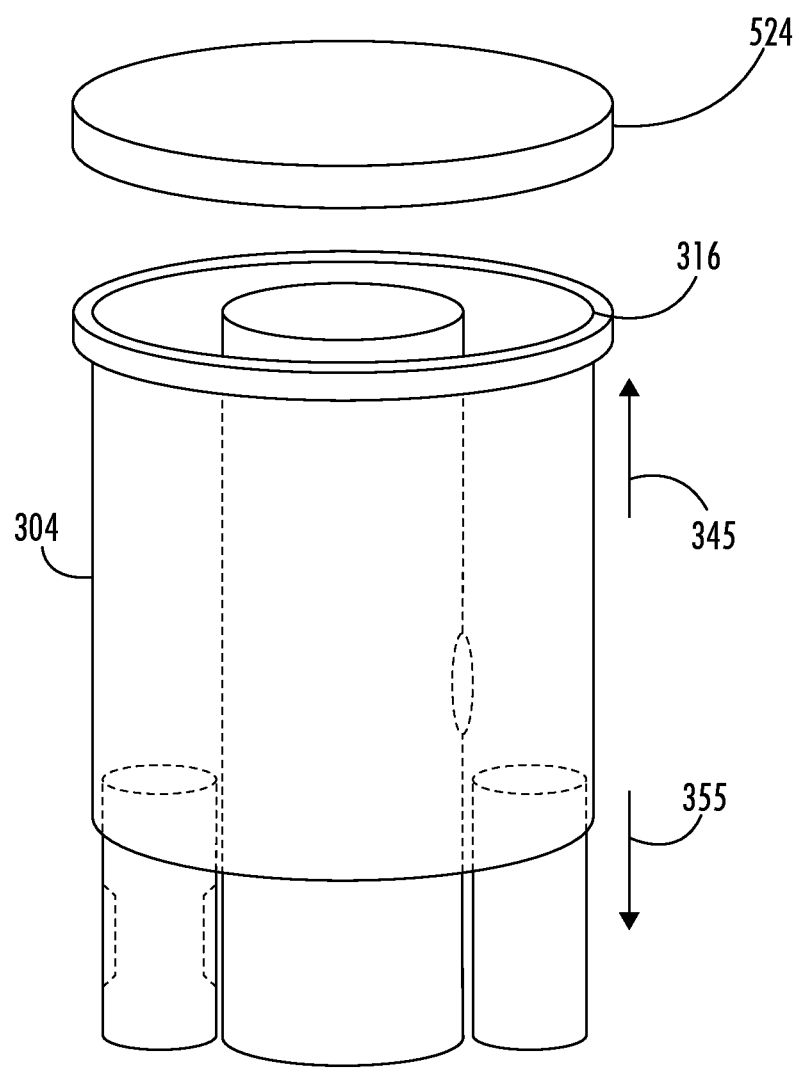
Figure 7B:
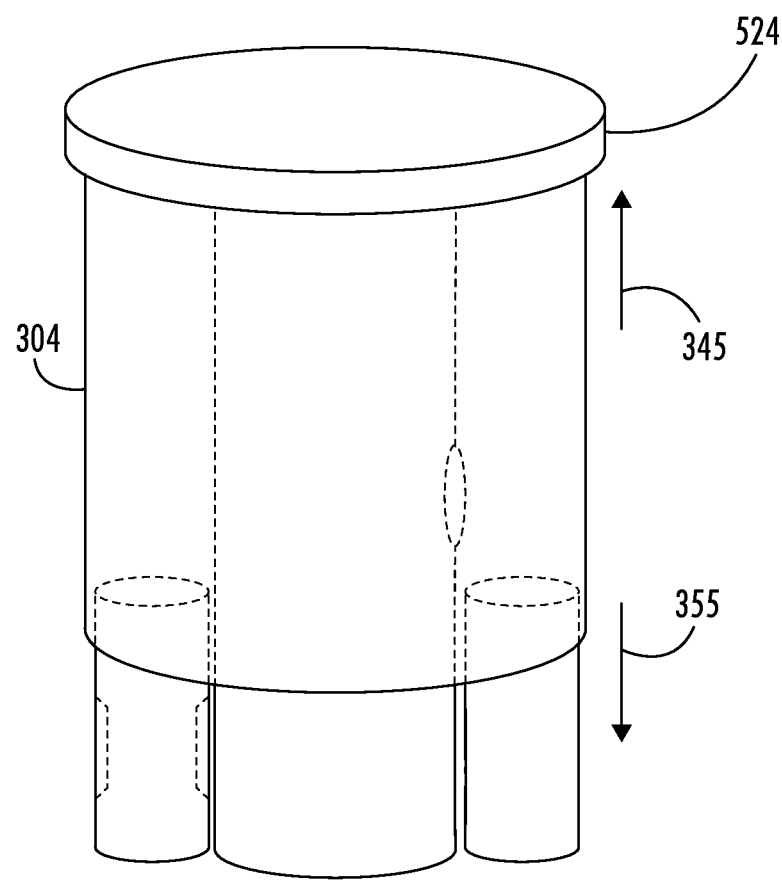

Referring to FIG. 7A, environment 700A illustrates an atmospheric valve open state 715-1. In the atmospheric valve open state 715-1, the atmospheric valve 524 may allow flow through the atmospheric channel 316 of suction valve well 304. Referring to FIG. 7B, environment 700B illustrates an atmospheric valve sealed state 715-2. In the atmospheric valve sealed state 715-2, the atmospheric valve 524 may prevent flow through atmospheric channel 316. As will be discussed in more detail below, in operation, fluid communication with the atmosphere may be provided through a passage/channel in, or created by, one or more components. Further, one or more components may be used to seal portions of the atmospheric channel 316 to facilitate control of fluid communication with the atmosphere by atmospheric valve 524. In some embodiments, atmospheric valve 524 may include a plurality of components configured to control fluid communication with the atmosphere.

Figure 8A:
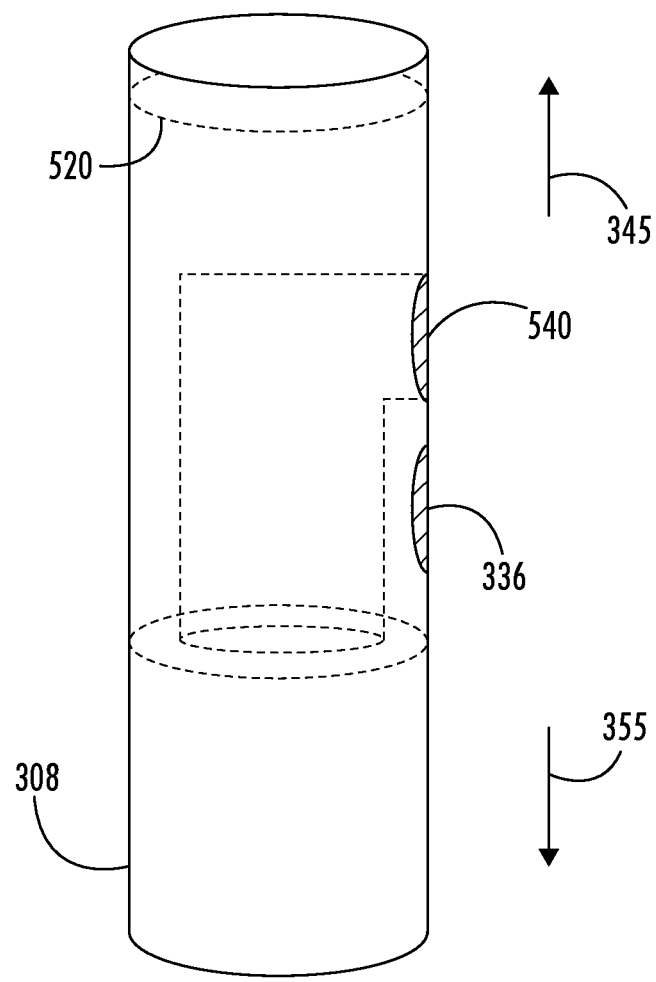
Figure 8B:
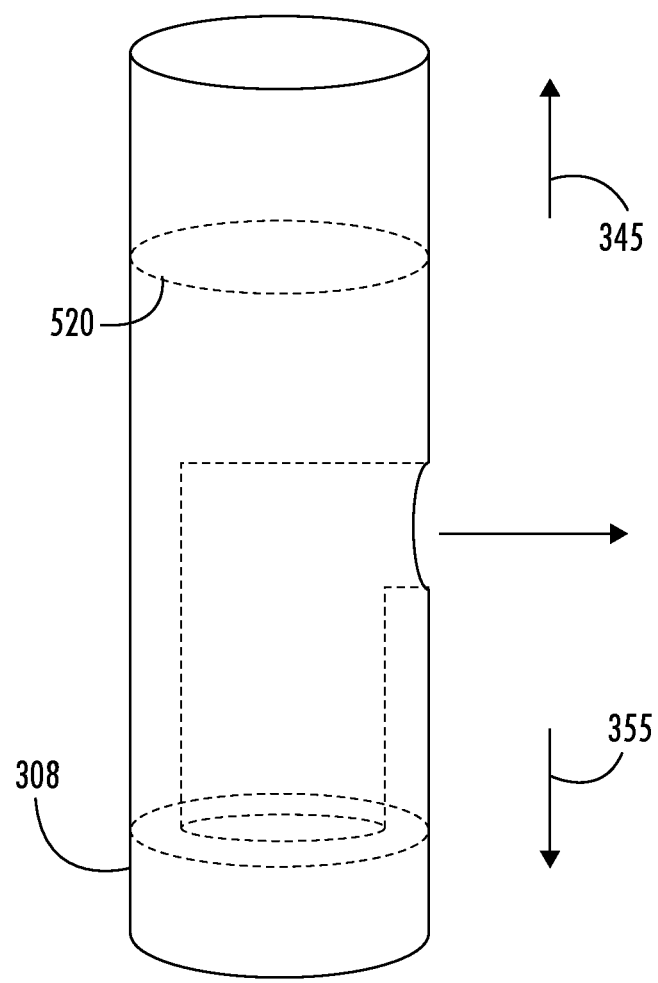
Figure 8C:
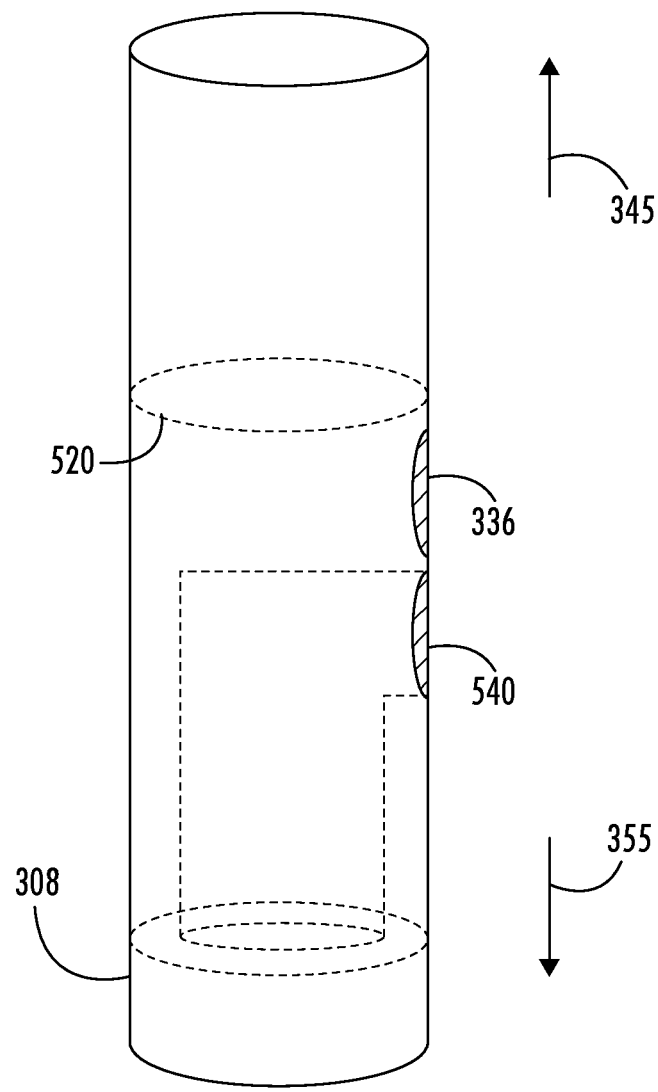

Referring to FIG. 8A, environment 800A illustrates a working channel valve first sealed state 815-1. In the working channel valve first sealed state 815-1, the working channel valve 520 may prevent flow through well radial hole 336 by misaligning the working channel valve radial hole 540 with the well radial hole 336, such as with working channel valve 520 being positioned such that working channel valve radial hole 540 is above well radial hole 336. Referring to FIG. 8B, environment 800B illustrates a working channel valve open state 815-2. In the working channel valve open state 815-2, the working channel valve radial hole 540 and the well radial hole 336 may be aligned to permit flow through working channel 308. Referring to FIG. 8C, environment 800C illustrates a working channel valve second sealed state 815-3. In the working channel valve second sealed state 815-3, the working channel valve 520 may prevent flow through well radial hole 336 by misaligning the working channel valve radial hole 540 with the well radial hole 336, such as with working channel valve 520 being positioned such that working channel radial hole 440 is below well radial hole 336.

Figure 9:
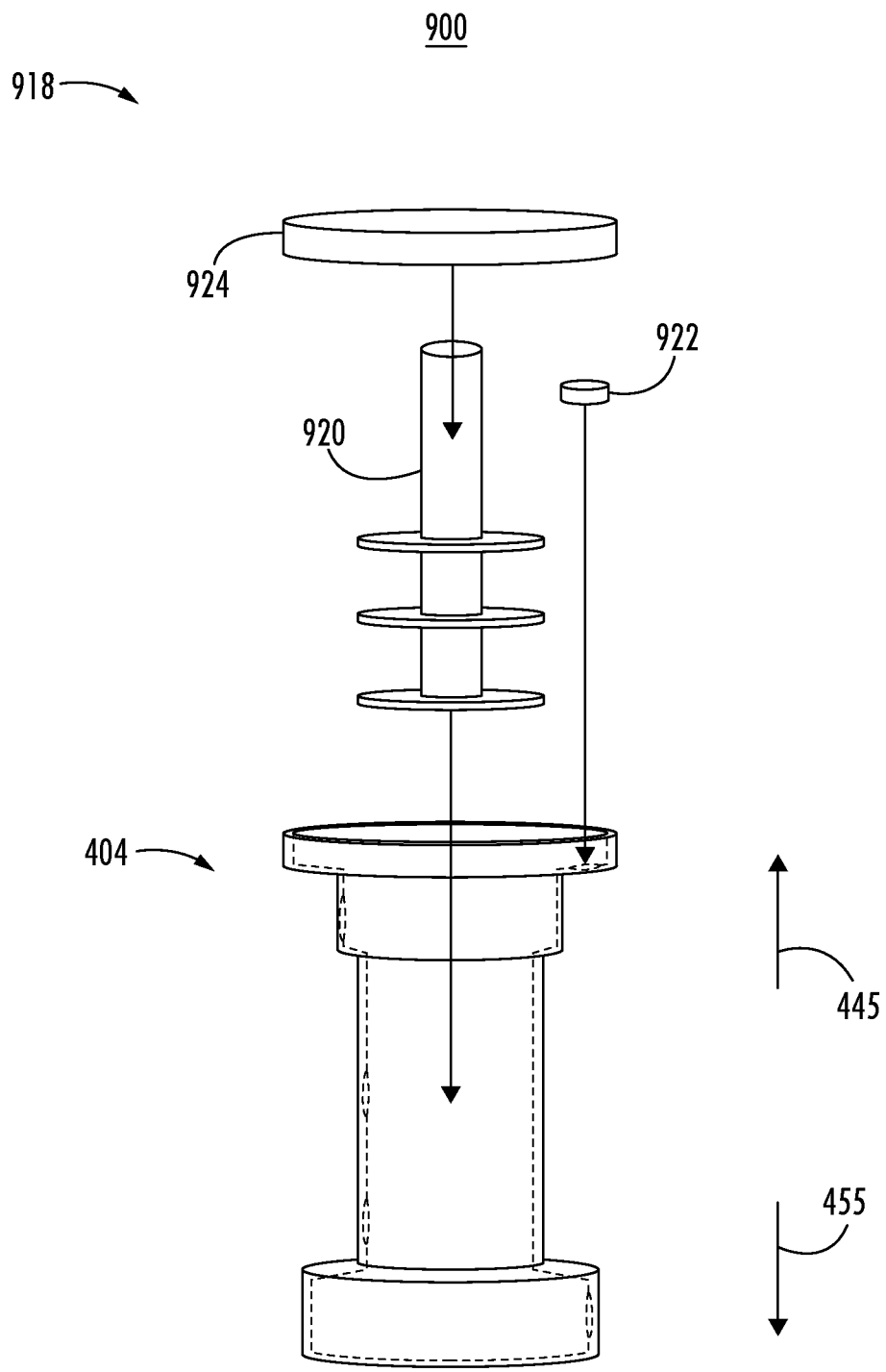
FIG. 9 illustrates an exemplary AW valve set, according to one or more embodiments described herein.

Referring to FIG. 9, environment 900 illustrates AW valve set 918 in conjunction with Aw valve well 404. Aw valve set 918 may include primary control valve 920, air input valve 922, and atmospheric valve 924. In several embodiments, the primary control valve 920 may be inserted into the AV valve well 404 to control, at least in part, the flow through one or more channels of the AW valve well 404. In various embodiments, the air input valve 922 may be inserted into the air input channel of the AW valve well 404 to control flow therethrough. In many embodiments, the atmospheric valve 924 may be inserted into the atmospheric channel of AW valve well 404 to control flow therethrough. In many embodiments, one or more valves in AW valve set 918 may be integrated with one or more portions of a housing and/or valve interface mechanism corresponding to AW valve well 404.

In one or more embodiments, the atmospheric valve 924 may be configured to control fluid communication with the atmosphere from the interior of the AW valve well 404. In many embodiments, the atmospheric valve 924 may include a hole in a housing. In some embodiments, the atmospheric valve 924 may be operated by covering and/or uncovering the hole, such as with a finger or other mechanism. In several embodiments, the positioning and/or configuration of the valves in AW valve set 918 may be controlled by one or FIGS. 1 and 2 illustrate block diagrams of exemplary valve assemblies in environments 100, 200, according to one or more embodiments described herein. In some embodiments, one or more components of environment 100 and/or environment 200 may be the same or similar to one or more other components described herein. Environment 100 may include a suction valve assembly 102 with a suction valve well 104, a suction valve set 118, and a valve interface mechanism 126. Environment 200 may include an air/water (AW) valve assembly 202 with an AW valve well 204, an AW valve set 218, and a valve interface mechanism 226. In one or more embodiments described herein, various components of suction valve assembly 102 and/or AW valve assembly 202 may interoperate to provide reliable and intuitive control of fluid flow through endoscopic systems. For example, one or more components of valve sets 118, 218 and valve interface mechanisms 126, 226 may provide reliable and intuitive control of fluid flow through suction valve well 104 or AW valve well 204. In many embodiments, components of a valve assembly may be classified as, belong to, include, implement, and/or interoperate with one or more of a valve well, a valve set, and a valve interface mechanism. For instance, a valve interface mechanism may include one or more portions of a valve. Embodiments are not limited in this context.

In environment 100, the suction valve well 104 may include suction channel 106, working channel 108, balloon channel 114, and atmospheric channel 116; the suction valve set 118 may include working channel valve 120, balloon valve 122, and atmospheric valve 124; and the valve interface mechanism 126 may include biasing member set 128 and user interface mechanism 130. In various embodiments, the channels of the suction well 104 may be connected to other components in an endoscopic system, such as via tubing or piping. In one or more embodiments described herein, the suction channel 106 may be connected to a suction source, the working channel 108 may be connected to a working channel of an endoscopic device (e.g., endoscope or component disposed therethrough), the balloon channel 114 may be connected to a balloon of an endoscopic device. In several embodiments, suction valve set 118 and valve interface mechanism 126 may control the flow of suction (e.g., induced by negative pressure relative to atmospheric pressure) through suction valve well 104. In several such embodiments, the flow of suction may be controlled to the suction channel 106 from one of the working channel 108, the balloon channel 114, and the atmospheric channel 116.

In environment 200, the AW valve well 204 may include air input channel 206, water input channel 208, air output channel 210, water output channel 212, balloon channel 214, and atmospheric channel 216; the AW valve set 218 may include primary control valve 220, air input valve 222, and atmospheric valve 224; and the valve interface mechanism 226 may include biasing member set 228 and user interface mechanism 230. In various embodiments, the channels of the AW well 204 may be connected to other components in an endoscopic system, such as via tubing or piping. In one or more embodiments described herein, the air input channel 206 may be connected to a pressurized air source, the water input channel 208 may be connected to a water source, the air output channel 210 may be connected to an air channel of an endoscopic device (e.g., endoscope or component disposed therethrough), the water output channel 212 may be connected to a water channel of an endoscopic device, and the balloon channel 214 may be connected to a balloon of an endoscopic device. In several embodiments, AW valve set 218 and valve interface mechanism 226 may control the flow of air and water through AW valve well 204. In several such embodiments, the flow of air may be controlled from air input channel 206 to one of the air output channel 210, the atmospheric channel 216, or blocked, and/or the flow of water may be controlled from water input channel 208 to one of water output channel 212, the balloon channel 214, or blocked.

In many embodiments, suction valve assembly 102 and/or AW valve assembly 202 may be used in conjunction with an endoscopic system, such as an EUS system. In various embodiments, reference to a balloon may refer to a balloon in the EUS system that can be inflated/deflated to provide medium to facilitate transmission of sound waves and capturing of ultrasound images. For example, valve interface mechanism 126 may receive input to control the flow through suction valve well 104 to deflate the balloon by arranging the suction valve set 118 to place the suction channel 106 in fluid communication with the balloon channel 114. In another example, valve interface mechanism 226 may receive input to control the flow of water through AW valve well to inflate the balloon by arranging the AW valve set 218 to place the water input channel 208 in fluid communication with balloon channel 214. In other embodiments, one or more of the components of the valve assembly for AW and/or suction may be implemented in configurations that do not require or include a balloon, such as video capable scope with ultrasound functionality.

More generally, in several embodiments, each channel in a valve well may refer to a flow path comprising an input/output of a fluid from/to a corresponding entity. For example, suction channel 106 may refer to a flow path comprising an input from a suction source. In another example, an atmospheric channel may refer to a flow path comprising an output to the atmosphere. These and other aspects of the present disclosure will be described in more detail below, such as with respect to FIGS. 3A-4E. In various embodiments, each valve in a valve set may refer to a component that physically controls flow through or between one or more channels. For instance, when closed, the atmospheric valve 124 may block the flow of air out of the atmospheric channel 116. In another instance, in a first position, or first state, the primary control valve 220 may place the water input channel 208 in fluid communication with the water output channel 212, and in a second position, the primary control valve 220 may place the water input channel 208 in fluid communication with the balloon channel 214. These and other aspects of the present disclosure will be described in more detail below, such as with respect to FIGS. 5-12C.

In various embodiments, the valve interface mechanisms may include one or more components to enable control over the arrangement of valves in a valve set. In such embodiments, biasing member sets may include one or more, torsional springs, lever springs, coil spring, baffles, dampers, clips, and the like that provide a force to bias one or more components in a specific direction or position. For example, the biasing member set 228 may cause air to flow out the atmospheric channel when no input is being received. In an additional, or alternative example, the biasing member set 128 may provide differing resistance to operation of the user interface mechanism 130 between different states, such as to provide tactile indications of the state. In various embodiments, each of the user interface mechanisms 130, 230 may include one or more of an interface, an interface member, a user interface, a housing, a linkage, a knob, a lever, a rocker switch, a push/pull switch, a knob, a button, a diaphragm switch, a toggle switch, and the like. In some embodiments, an interface, an interface member, and/or a user interface may be the same or similar.

In several embodiments, user interface mechanisms may include one or more components to receive input and/or implement valve arrangements. For example, user interface mechanism 130 may include a user interface comprising a lever and one or more linkages to translate motion of the lever into appropriate motion of one or more valves to achieve a desired flow. In various embodiments, user interface mechanisms may include one or more biasing members and/or biasing members may include one or more user interface mechanisms. It will be appreciated that one or more components described herein in the context of a suction valve assembly may be utilized in or adapted for use in an AW valve assembly, and vice versa, without departing from the scope of this disclosure. For example, a rotational user interface mechanism described with respect to a suction valve interface mechanism may be utilized in or adapted for use in an AW valve interface mechanism. These and other aspects of the present disclosure will be described in more detail below.

FIGS. 3A-4E illustrate various aspects of exemplary valve well block diagrams of exemplary valve assemblies in environments 300A-D, 400A-E, according to one or more embodiments described herein. In some embodiments, one or more components of FIGS. 3A-4E may be the same or similar to one or more other components described herein. Environments 300A-D illustrate a suction valve well 304 comprising a suction channel 306, a working channel 308, a balloon channel 314 and an atmospheric channel 315. Environments 400A-E illustrate an AW valve well 404 with an air input channel 406, a water input channel 408, an air output channel 210, a water output channel 212, a balloon channel 214, and an atmospheric channel 216. In one or more embodiments described herein, fluid may flow through the valve wells based on the arrangement of one or more valves as positioned by one or more valve interface mechanisms. Embodiments are not limited in this context.

Referring to FIG. 3A, environment 300A illustrates various components of suction valve well 304. The suction valve well 304 may include a top 345 and a bottom 335. The suction channel 306, working channel 308, and balloon channel 314 may comprise respective entrances/exits towards the bottom 355 while the atmospheric channel 316 may comprise an entrance towards the top 345. In the illustrated embodiment, the balloon channel 314 includes a necking portion 334, the working channel 308 includes a well radial hole 336, and the atmospheric channel 316 includes a lip 332. In one or more embodiments, the necking portion 334 may enable a valve to prevent fluid flow through the balloon channel 314, such as by blocking the necking portion 334. In various embodiments, the well radial hole 336 may enable the working channel 308 to be placed in fluid communication with the suction channel 306. In several embodiments, the lip 332 may enable one or more suction valve sets and/or valve interface mechanisms to couple to the suction valve well 304. In many embodiments, valves and/or valve interface mechanisms may be inserted through atmospheric channel 316 for assembly of a suction valve assembly. It will be appreciated that the orientation and/or arrangement of one or more of the channels and/or flows may be modified in various embodiments without departing from the scope of this disclosure.

Referring to FIG. 3B, environment 300B illustrates a flow 338-1 through the suction valve well 304 in an atmospheric suction state 305-1. In the atmospheric suction state 305-1, flow 338-1 may enter via the atmospheric channel 316 and exit through the suction channel 306. For example, suction channel 306 may be an input in the handle of a medical scope that is connected to a vacuum system, such as for a hospital, home, and/or mobile device.

Further, in some embodiments, flow may be blocked through the balloon channel 314 at the necking portion 334 and flow may be blocked through the working channel 308 at the well radial hole 336. As will be discussed in more detail below, in operation, fluid communication with the atmosphere may be provided through a passage/channel in, or created by, one or more components (e.g., a valve inserted into the atmospheric channel 316). Further, one or more components may be used to seal portions of the atmospheric channel 316 to facilitate blocking of fluid communication with the atmosphere by an atmospheric valve.

Referring to FIG. 3C, environment 300C illustrates a flow 338-2 through the suction valve well 304 in a working channel suction state 305-2. In the working channel suction state 305-2, flow 338-2 may enter via the working channel 308, pass through the well radial hole 336, and exit through the suction channel 306. Further, in many embodiments, flow may be blocked through the balloon channel 314 at the necking portion 334 and flow may be blocked through the atmospheric channel 316.

Referring to FIG. 3D, environment 300D illustrates a flow 338-3 through the suction valve well 304 in a balloon channel suction state 305-3. In the balloon channel suction state 305-3, flow 338-3 may enter via the balloon channel 314 and exit through the suction channel 306. Further, in several embodiments, flow may be blocked through the working channel 308 at the well radial hole 336 and may be blocked through the atmospheric channel 316.

Referring to FIG. 4A, environment 400A illustrates various components of AW valve well 404. The AW valve well 404 may include a top 445 and a bottom 435 and/or an air portion 425 and a water portion 435. The air output channel 410, air input channel 412, and atmospheric channel 416 may be in the air portion 425. The atmospheric channel 416 may comprise a horizontally-oriented exit towards the top 345 and lip 432, the air input channel 412 may comprise a horizontally-oriented entrance towards the top 345, the air output channel 410 may comprise a vertically-oriented exit towards the top. The water input channel 408, water output channel 412, and balloon channel 414 may be in the water portion 435. The balloon channel 414 may comprise a vertically-oriented exit proximate the middle, the water input channel 408 may comprise a vertically-oriented entrance toward the bottom 455, and the water output channel 412 may comprise a vertically-oriented exit toward the bottom 455. In several embodiments, the lip 432 may enable one or more suction valve sets and/or valve interface mechanisms to couple to the AW valve well 404.

In several embodiments, the AW valve well 404 may change diameters one or more times. For example, the diameter changes in conjunction with vertical displacement of a valve may enable flow around the valve and through a channel. In the illustrated embodiment, the AW valve well may have a first diameter comprising the entrance/exits of the air input/atmospheric channels 412, 416, a second diameter comprising the exit of the air output channel 410, a third diameter comprising the entrance/exit of the water input/balloon channels 408, 414, and a fourth diameter comprising the exit of the water output channel 412. It will be appreciated that the orientation, size, and/or arrangement of one or more of the channels and/or flows may be modified in various embodiments without departing from the scope of this disclosure.

Referring to FIG. 4B, environment 400B illustrates a flow 438-1 through the AW valve well 404 in an air escape state 405-1. In the air escape state 405-1, flow 438-1 may enter via air input channel 406 and exit through the atmospheric channel 416. Further, in some embodiments, flow may be blocked through one or more of balloon channel 414, water input channel 408, and water output channel 412.

Referring to FIG. 4C, environment 400C illustrates a flow 438-2 through the AW valve well 404 in an air delivery state 405-2. In the air delivery state 405-2, flow 438-2 may enter via the air input channel 406 and exit through the air output channel 410. Further, in various embodiments, flow may be blocked through one or more of atmospheric channel 416, balloon channel 414, water input channel 408, and water output channel 412.

Referring to FIG. 4D, environment 400D illustrates a flow 438-3 through the AW valve well 404 in a water delivery state 405-3. In the water delivery state 405-3, flow 438-3 may enter via water input channel 408 and exit through the water output channel 412. Further, in various embodiments, flow may be blocked through one or more of the balloon channel 414, air output channel 410, air input channel 406, and atmospheric channel 416. In various embodiments, blocking flow at the air input channel 406 may cause pressure to build in a water source feeding the water input channel 408. In various such embodiments, pressure in the water source may cause fluid to flow from the water source to water input channel 408.

Referring to FIG. 4E, environment 400E illustrates a flow 438-4 through the AW valve well 404 in a balloon fill state 405-4. In the balloon fill state 405-4, flow 438-4 may enter via the water input channel 408 and exit through the balloon channel 414. Further, in many embodiments, flow may be blocked through one or more of the water output channel 412, air output channel 410, air input channel 406, and atmospheric channel 413.

FIGS. 5-12C illustrate various aspects of exemplary valve sets in environments 500, 600A, 600B, 700A, 700B, 800A-C, 900, 1000A, 1000B, 1100A, 1100B, 1200A-C, according to one or more embodiments described herein. In some embodiments, one or more components of FIGS. 5-12C may be the same or similar to one or more other components described herein. Environments 500-800C illustrate various aspects of a suction valve set 518 in conjunction with one or more components of suction valve well 304. Environments 900-1200C illustrate various aspects of an AW valve set 918 in conjunction with one or more components of AW valve well 404. In one or more embodiments described herein, fluid may flow through the valve wells based on the arrangement of one or more valves as positioned by one or more valve interface mechanisms. In many embodiments, one or more valves described herein may include a plurality of components configured to control fluid through a valve well. Embodiments are not limited in this context.

Referring to FIG. 5, environment 500 illustrates suction valve set 518 in conjunction with suction valve well 304. Suction valve set 518 may include working channel valve 520, balloon valve 522, and atmospheric valve 524. The working channel valve 520 may include a working channel valve radial hole 540 that enables fluid to flow into the working channel valve 520 out of the bottom of the working channel valve 520. In several embodiments, the working channel valve 520 may be inserted into the working channel of suction valve well 304 to control flow therethrough. The balloon valve 522 may be inserted into balloon channel 314 of suction valve well 304 to control flow therethrough. The atmospheric valve 524 may be inserted into the atmospheric channel of suction valve well 304 to control flow therethrough. In many embodiments, one or more valves in suction valve set 518 may be integrated with one or more portions of a housing and/or valve interface mechanism corresponding to suction valve well 304.

In one or more embodiments, the atmospheric valve 524 may be configured to control fluid communication with the atmosphere from the interior of the suction valve well 304. In many embodiments, the atmospheric valve 524 may include a hole in a housing. In some embodiments, the atmospheric valve 524 may be operated by covering and/or uncovering the hole, such as with a finger or other mechanism. In several embodiments, the positioning and/or configuration of the valves in suction valve set 518 may be controlled by one or more components of a corresponding valve interface mechanism. For example, depressing a valve interface mechanism to a first stop may simultaneously shut off atmospheric suction via a seal on the underside of a cap and open working channel suction by pushing down the center of the working channel valve 520 to align the working channel valve radial hole 540 and the well radial hole.

Referring to FIG. 6A, environment 600A illustrates a balloon valve open state 615-1. In the balloon valve open state 615-1, the balloon valve 522 may allow flow through the balloon channel 314 by permitting flow through the necking portion 334 of balloon channel 314. Referring to FIG. 6B, environment 600B illustrates a balloon valve sealed state 615-2. In the balloon valve sealed state 615-2, the balloon valve 522 may prevent flow through balloon channel 314 by blocking flow through the necking portion 334 of balloon channel 314. In additional, or alternative embodiments, the default state of the balloon valve 522 may be the balloon valve sealed state 615-2 and the balloon valve 522 may be depressed toward the bottom 355 and below the necking portion 334 to transition into the balloon valve open state 615-1.

Referring to FIG. 7A, environment 700A illustrates an atmospheric valve open state 715-1. In the atmospheric valve open state 715-1, the atmospheric valve 524 may allow flow through the atmospheric channel 316 of suction valve well 304. Referring to FIG. 7B, environment 700B illustrates an atmospheric valve sealed state 715-2. In the atmospheric valve sealed state 715-2, the atmospheric valve 524 may prevent flow through atmospheric channel 316. As will be discussed in more detail below, in operation, fluid communication with the atmosphere may be provided through a passage/channel in, or created by, one or more components. Further, one or more components may be used to seal portions of the atmospheric channel 316 to facilitate control of fluid communication with the atmosphere by atmospheric valve 524. In some embodiments, atmospheric valve 524 may include a plurality of components configured to control fluid communication with the atmosphere.

Referring to FIG. 8A, environment 800A illustrates a working channel valve first sealed state 815-1. In the working channel valve first sealed state 815-1, the working channel valve 520 may prevent flow through well radial hole 336 by misaligning the working channel valve radial hole 540 with the well radial hole 336, such as with working channel valve 520 being positioned such that working channel valve radial hole 540 is above well radial hole 336. Referring to FIG. 8B, environment 800B illustrates a working channel valve open state 815-2. In the working channel valve open state 815-2, the working channel valve radial hole 540 and the well radial hole 336 may be aligned to permit suction flow through working channel 308. For example, the flow may enter through the bottom of the working channel valve 520 and exit through the well radial hole 336. Referring to FIG. 8C, environment 800C illustrates a working channel valve second sealed state 815-3. In the working channel valve second sealed state 815-3, the working channel valve 520 may prevent flow through well radial hole 336 by misaligning the working channel valve radial hole 540 with the well radial hole 336, such as with working channel valve 520 being positioned such that working channel valve radial hole 440 is below well radial hole 336.

Referring to FIG. 9, environment 900 illustrates AW valve set 918 in conjunction with AW valve well 404. AW valve set 918 may include primary control valve 920, air input valve 922, and atmospheric valve 924. In several embodiments, the primary control valve 920 may be inserted into the AW valve well 404 to control, at least in part, the flow through one or more channels of the AW valve well 404. In various embodiments, the air input valve 922 may be inserted into the air input channel of the AW valve well 404 to control flow therethrough. In many embodiments, the atmospheric valve 924 may be inserted into the atmospheric channel of AW valve well 404 to control flow therethrough. In many embodiments, one or more valves in AW valve set 918 may be integrated with one or more portions of a housing and/or valve interface mechanism corresponding to AW valve well 404.

In one or more embodiments, the atmospheric valve 924 may be configured to control fluid communication with the atmosphere from the interior of the AW valve well 404. In many embodiments, the atmospheric valve 924 may include a hole in a housing. In some embodiments, the atmospheric valve 924 may be operated by covering and/or uncovering the hole, such as with a finger or other mechanism. In several embodiments, the positioning and/or configuration of the valves in AW valve set 918 may be controlled by one or more components of a corresponding valve interface mechanism. In some embodiments, one or more portions of the atmospheric channel 416 may be included in the primary control valve 920. In some such embodiments, the atmospheric channel 416 may comprise one or more passages through at least a portion of the primary control valve 920. For example, the atmospheric channel 416 may comprise a hole in the top of the primary control valve 920 in fluid communication with a radial hole in the primary control valve 920 proximate the air input channel 406. In such examples, covering the hole may direct air flow into the air output channel 410 and down a working channel of an endoscope.

Figure 10A:
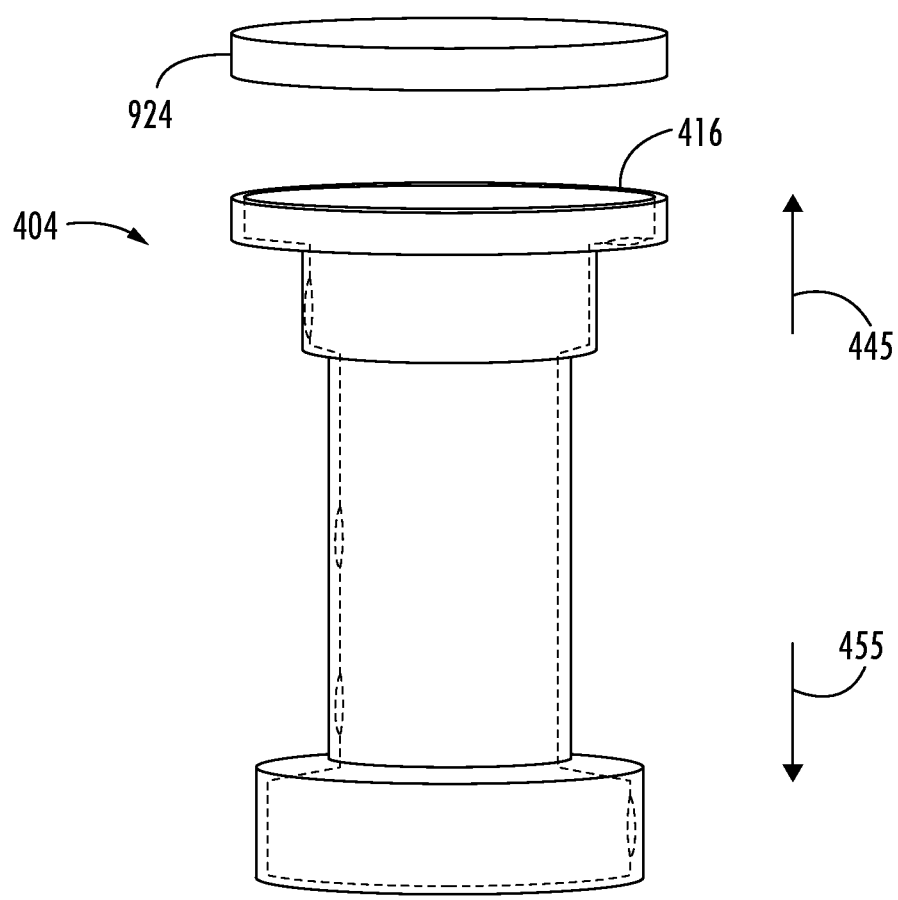
FIGS. 10A-12C illustrate various aspects of exemplary valves in AW valve sets, according to one or more embodiments described herein.
Figure 10B:
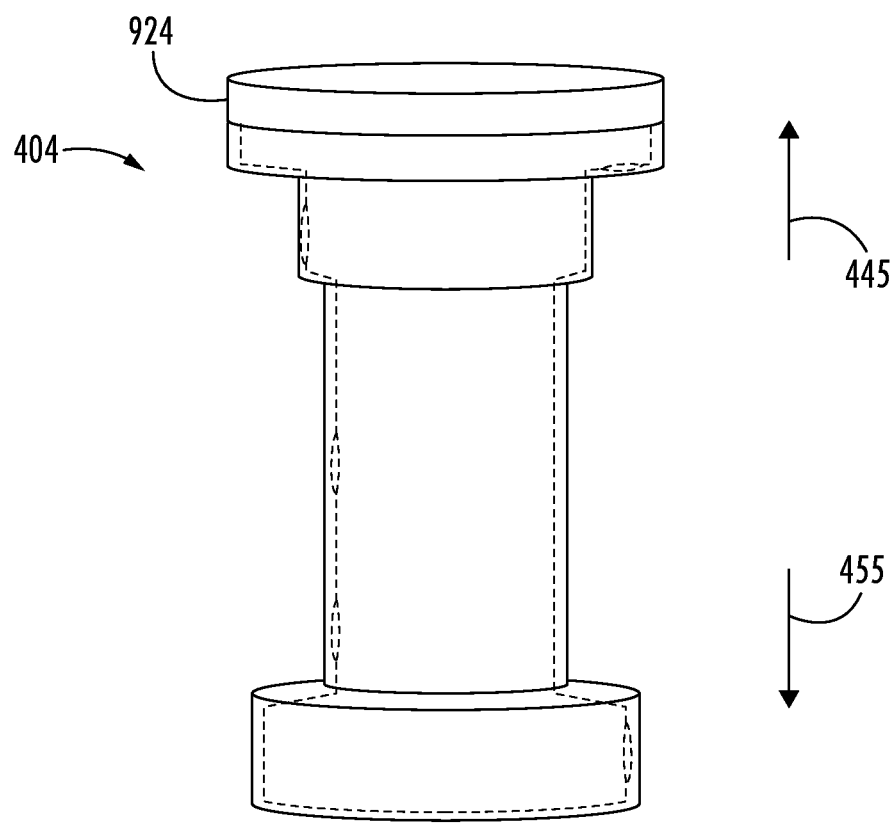

Referring to FIG. 10A, environment 1000A illustrates an atmospheric valve open state. In the atmospheric valve open state, the atmospheric valve 924 may allow flow through the atmospheric channel of AW valve well 404. Referring to FIG. 10B, environment 1000B illustrates an atmospheric valve sealed state 1015-2. In the atmospheric valve sealed state 1015-2, the atmospheric valve 924 may prevent flow through atmospheric channel of AW valve well 404. As will be discussed in more detail below, in operation, fluid communication with the atmosphere may be provided through a passage/channel in, or created by, one or more components (e.g., primary control valve 920). Further, one or more components may be used to seal portions of the atmospheric channel 316 to facilitate control of fluid communication with the atmosphere by atmospheric valve 924. In some embodiments, atmospheric valve 924 may include a plurality of components configured to control fluid communication with the atmosphere.

Figure 11A:
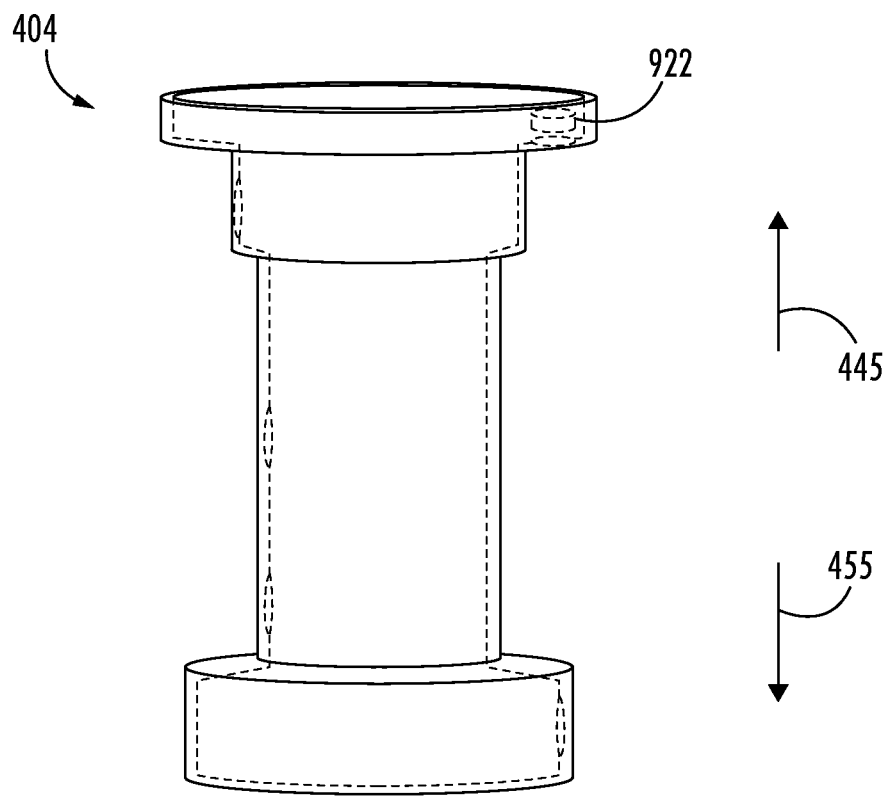
Figure 11B:
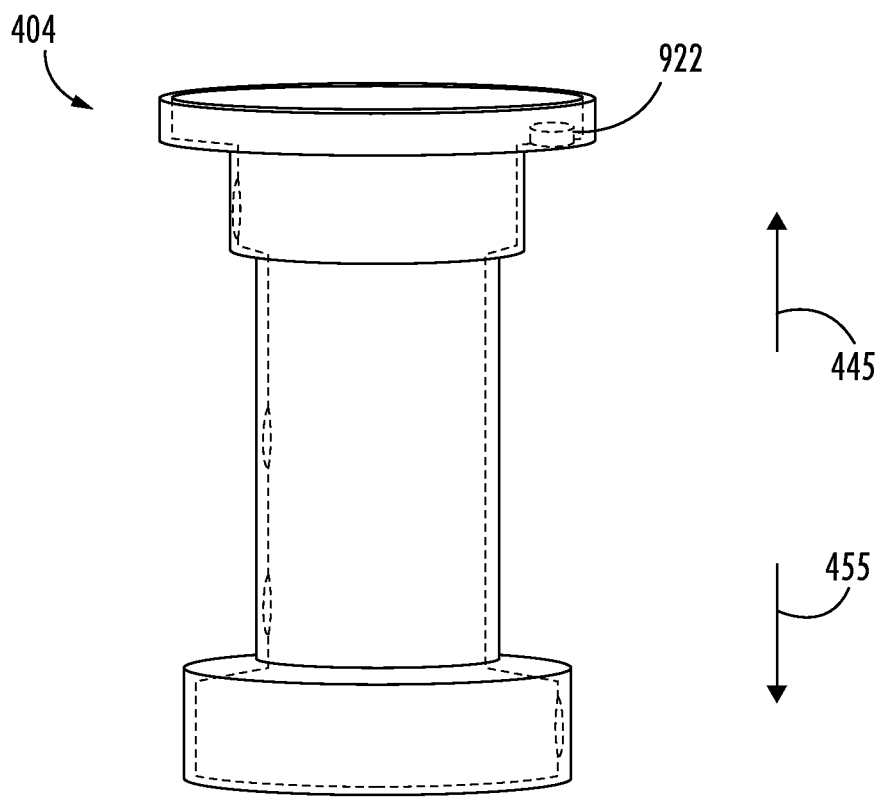

Referring to FIG. 11A, environment 1100A illustrates an air input valve open state 1115-1. In the air input valve open state 1115-1, the air input valve 522 may allow flow through the air input channel of AW valve well 404. Referring to FIG. 11B, environment 1100B illustrates an air input valve sealed state 1115-2. In the air input valve sealed state 1115-2, the air input valve 922 may prevent flow through the air input channel of AW valve well 404. In some embodiments, sealing the air input channel may cause a fluid source (e.g., water reservoir) to be pressurized, thereby enabling/causing fluid to flow into the AW valve well 404 via water input channel 408.

Figure 12A:
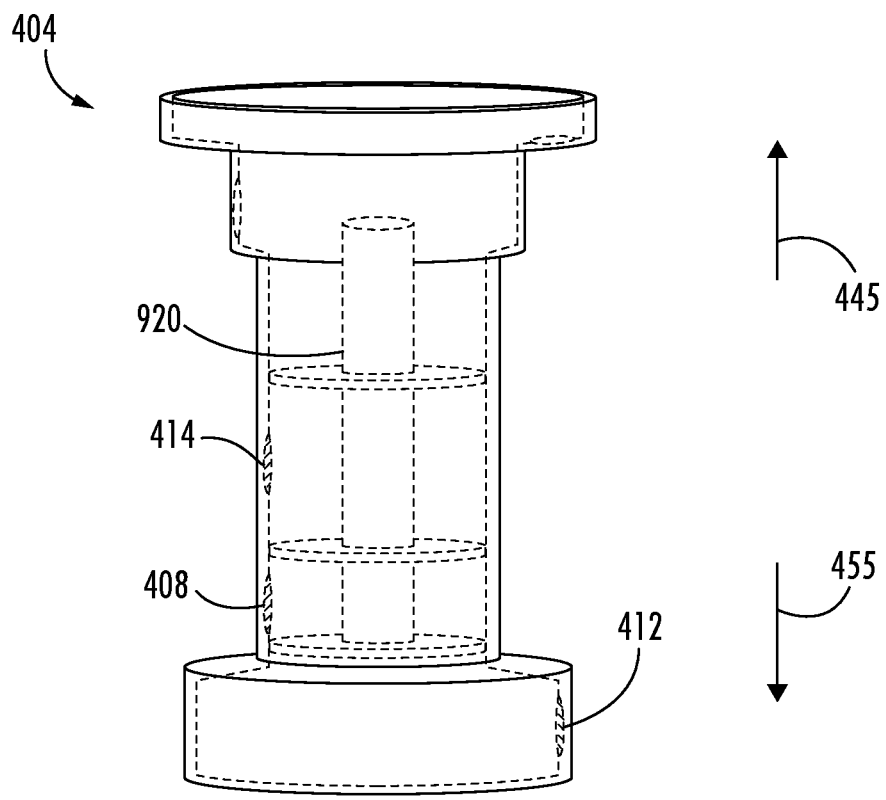
Figure 12B:
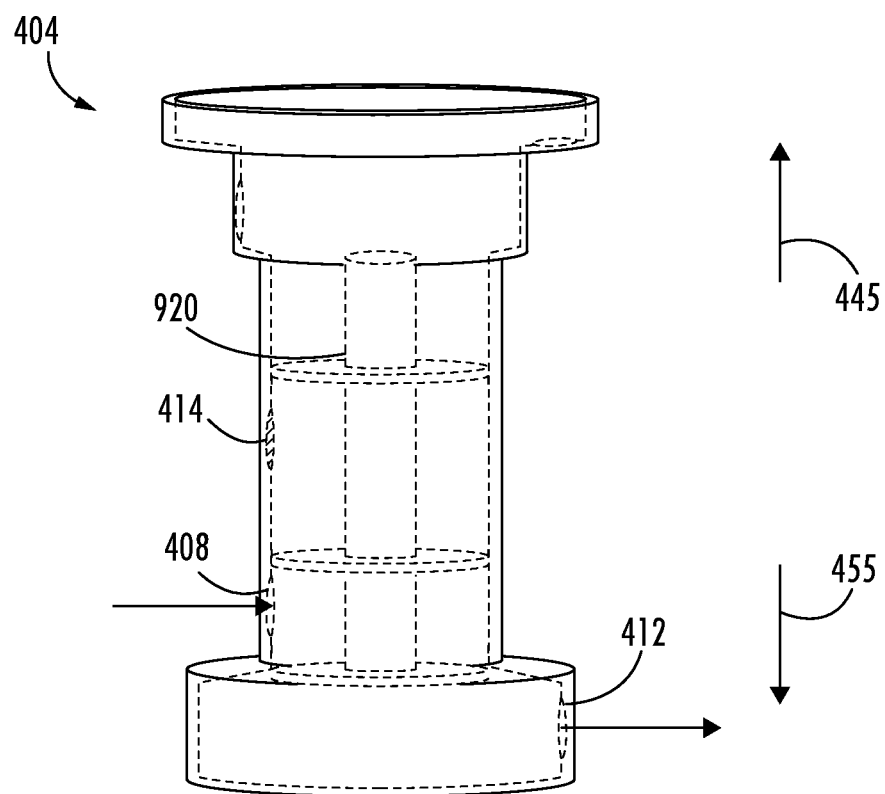
Figure 12C:
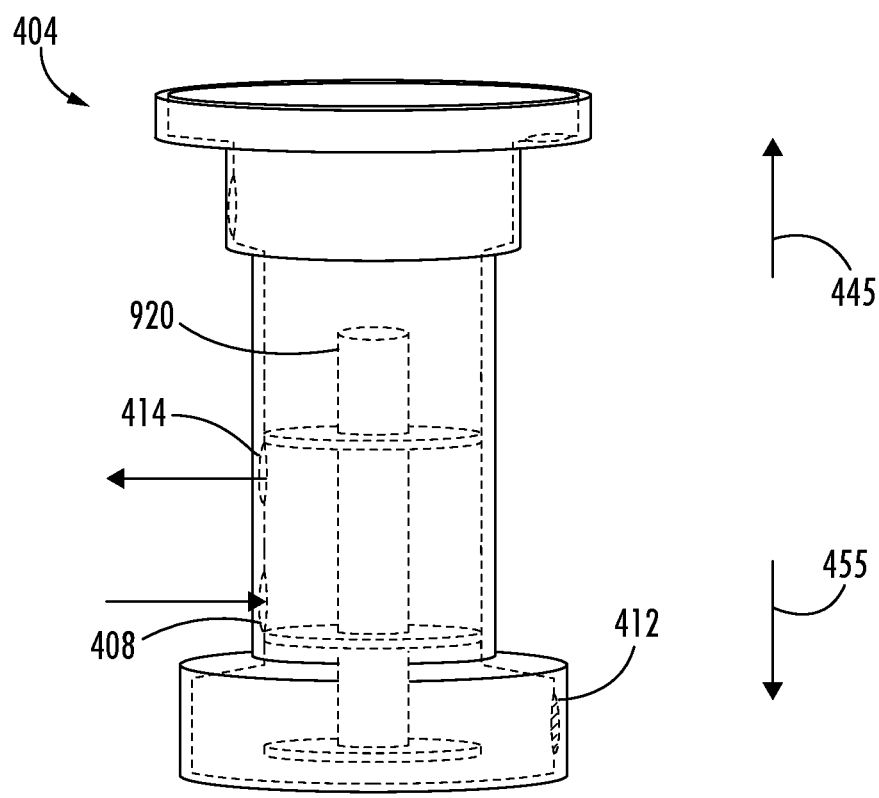

Referring to FIG. 12A, environment 1200A illustrates a primary valve sealed state 1215-1. In the primary valve sealed state 1215-1, the primary control valve 920 may prevent flow through one or more of the balloon channel 414, water input channel 408, and water output channel 412. Referring to FIG. 12B, environment 1200B illustrates a primary valve water output state 1215-2. In the primary valve water output state 1215-2, the primary control valve 920 may be positioned to block flow through balloon channel 414 and permit flow from water input channel 408 to water output channel 412. In various embodiments, primary control valve 920 may utilize changes in diameter in AW valve well 404 to control flow. Referring to FIG. 12C, environment 1200C illustrates a primary valve balloon fill state 1215-3. In the primary valve balloon fill state 1215-3, the primary control valve 920 may be positioned to block flow through water output channel 412 and permit flow from water input channel 408 to balloon channel 414. In various embodiments, one or more features of primary control valve 920 may operate as valves for multiple channels. In some embodiments, one or more features of primary control valve 920 may comprise one or more channels, or one or more portions thereof. For example, primary control valve 920 may comprise atmospheric channel 416.

Figure 13A:
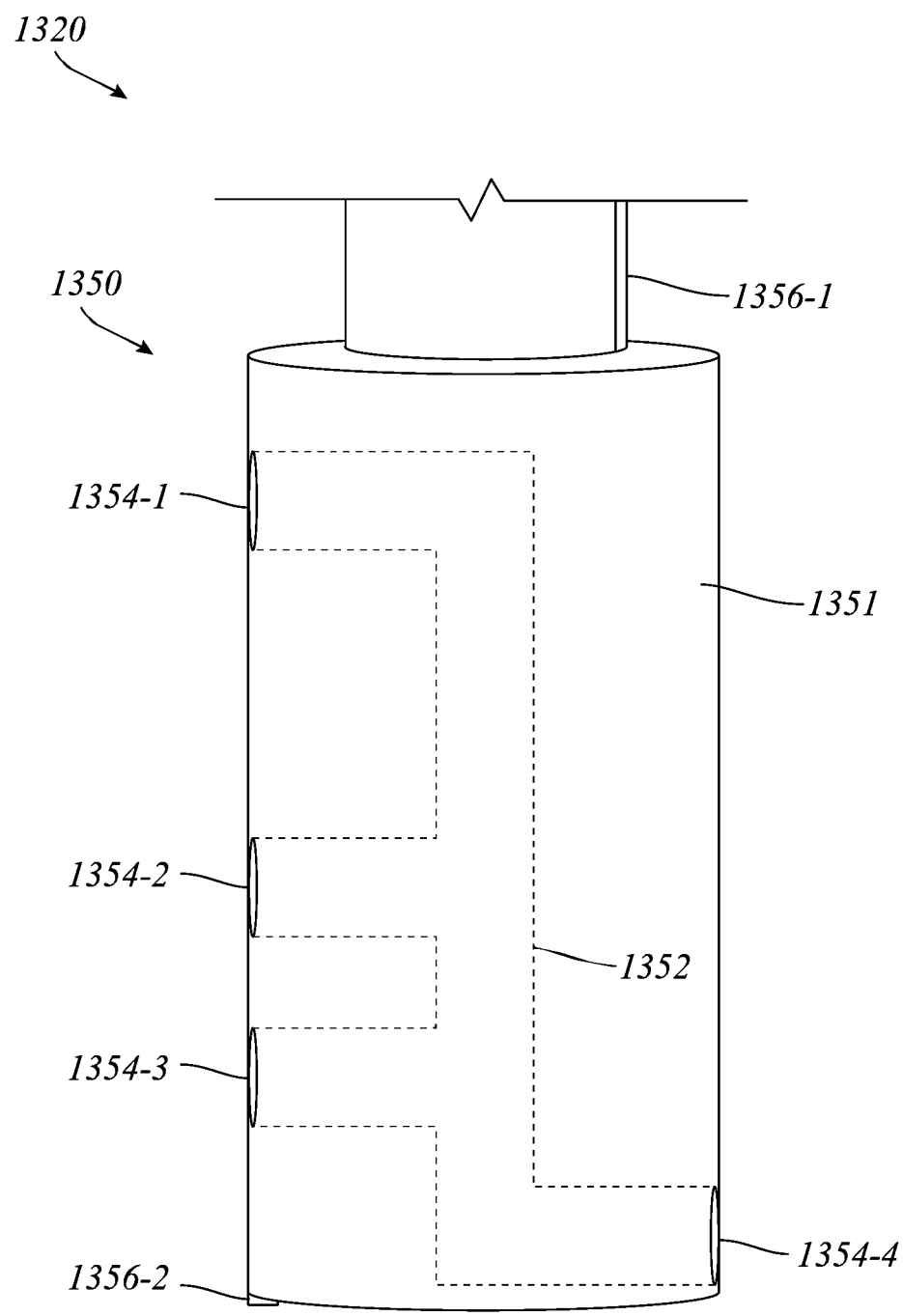
FIGS. 13A-13C illustrate various aspects of an exemplary primary control valve, according to one or more embodiments described herein.
Figure 13B:
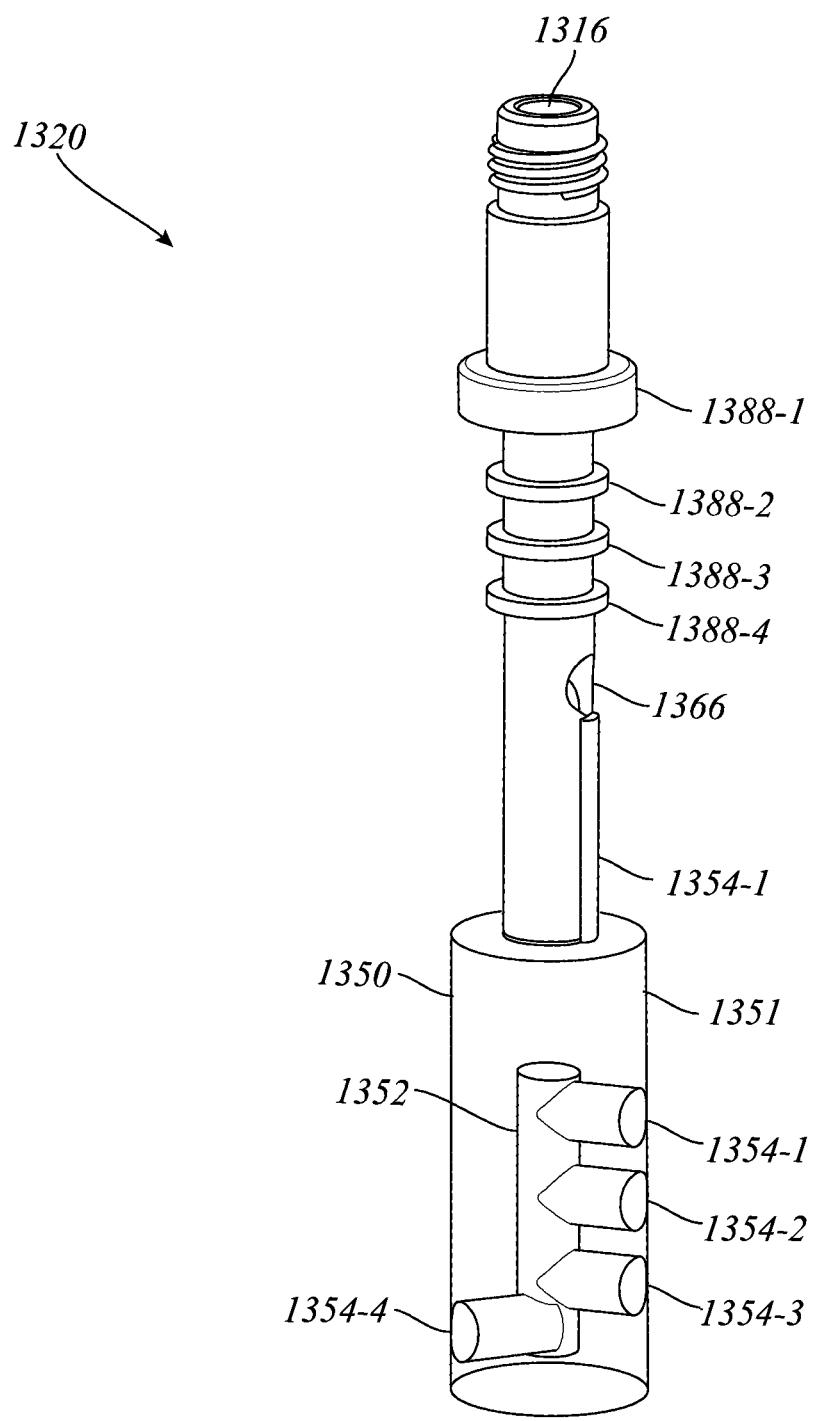
Figure 13C:
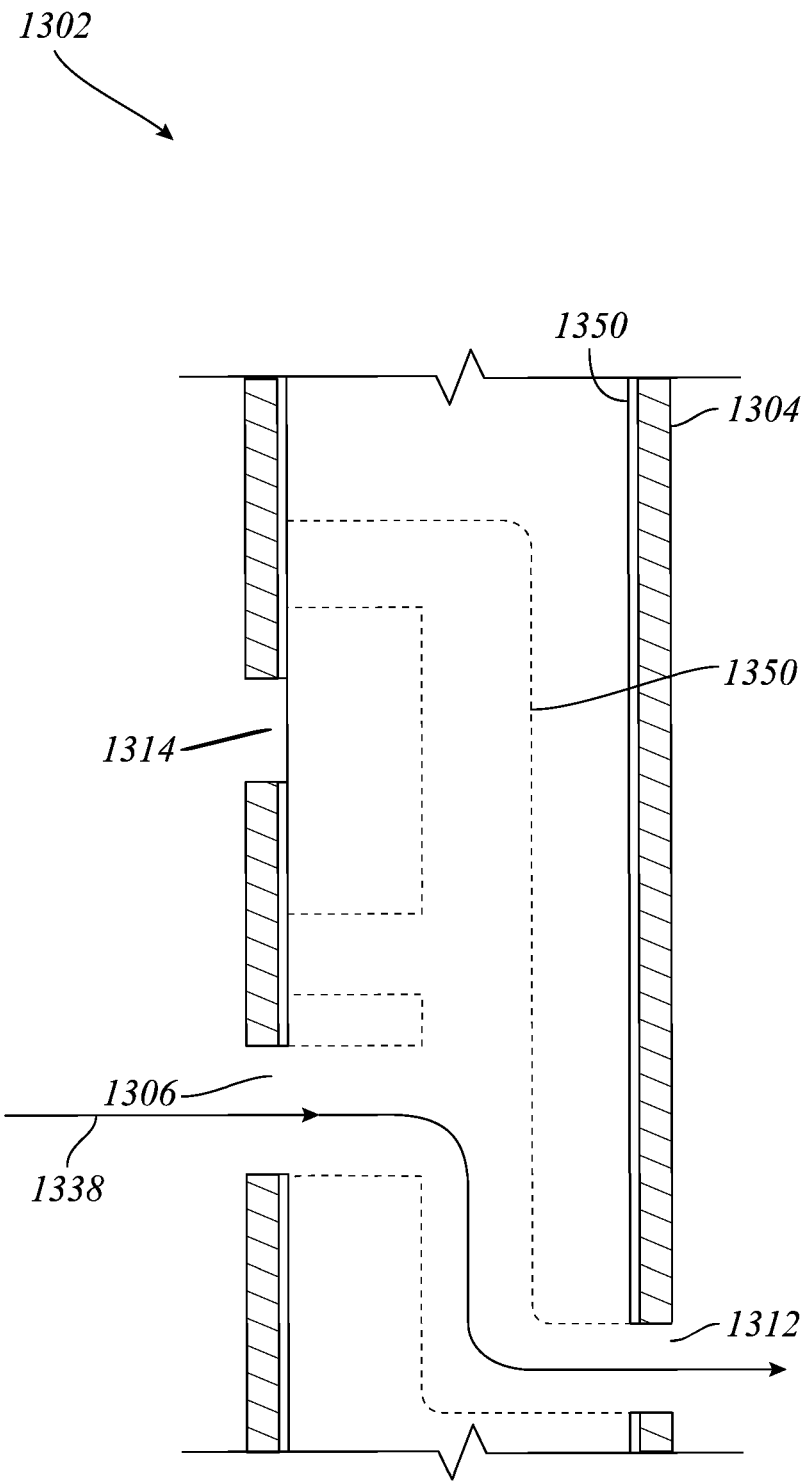

FIGS. 13A-13C illustrate various aspects of an exemplary primary control valve 1320 in environments 1300A, 1300B, 1300C, according to one or more embodiments described herein. In many embodiments, a cross section of one or more components may be illustrated in environments 1300A, 1300B, 1300C. In some embodiments, one or more components of FIGS. 13A-13C may be the same or similar to one or more other components described herein. In environment 1300A, the illustrated portion of primary control valve 1320 may include a valve body 1350 and alignment features 1356-1, 1356-2. Further, the valve body 1350 may include outer surface 1351, one or more manifold channels 1352, and manifold ports 1354-1, 1354-2, 1354-3, 1354-4 (or manifold ports 1354). In environment 1300B, the primary control valve 1320 may include atmospheric channel 1316, radial air hole 1366, alignment feature 1354-1, valve body 1350, and features 1388-1, 1388-2, 1388-3, 1388-4 (or features 1388). Further, the valve body 1350 may include outer surface 1351 (illustrated with transparent side portions in FIG. 13B), one or more manifold channels 1352 (illustrated as opaque in FIG. 13B), and manifold ports 1354-1, 1354-2, 1354-3, 1354-4 (or manifold ports 1354). In environment 1300C, valve body 1350 is shown in conjunction with AW valve well 1304 as part of AW valve assembly 1302. The illustrated portion of the AW valve well 1304 includes balloon channel 1314, water input channel 1306, and water output channel 1312. In many embodiments, the one or more manifold channels 1350 may place the manifold ports 1354 in fluid communication. In one or more embodiments described herein, the valve body 1350 of primary control valve 1320 may be vertically displaced and/or rotated to control the flow of fluid through a valve well 1304. Embodiments are not limited in this context.

Referring to environment 1300A, in various embodiments, primary control valve 1320 may include the valve body 1350 with one or more ports designed to be aligned with one or more channels of a valve well to control flow through the valve well. In many embodiments, the primary control valve may include one or more alignment features to guide installation and/or assembly of a valve assembly. In various embodiments, the alignment features may include mating portions of the primary control valve 1320 to one or more other components of the valve assembly, such as a portion of the valve body mating with a portion the valve well. Sometimes, the alignment feature may guide movement of one or more portions of the primary control valve 1320. Alignment feature 1356-2 may be disposed on valve body 1350. In some embodiments, the alignment features may utilize one or more features of the valve well (e.g., clocking holes and/or a snap fit into the air input channel).

Referring to environment 1300B, in many embodiments, primary control valve 1320 may include one or more features that are configured to enable the primary control valve to interoperate with other components of a valve assembly. For example, feature 1388-1 may provide a bearing or coupled point for a biasing member, such as a spring. In another example, a radial seal may be disposed between features 1388-2, 1388-3 to create a seal with one or more components of a valve well and/or valve interface mechanism. In many such examples, this seal may facilitate controlling the flow of fluid through a valve well. In some embodiments, radial air hole 1366 may be in fluid communication with atmospheric channel 1316. In some such embodiments, primary control valve 1320 may include a threaded section proximate the atmospheric channel 1316 to enable coupling of an atmospheric valve and/or valve interface mechanism. In some embodiments, one or more features of the primary control valve may couple to a linkage, bowl, and/or hat component.

Referring to environment 1300C, in several embodiments, valve body 1350 may utilize a solid shaft manufactured to sufficient precision to control flow through a valve well. In various embodiments, the valve body 1350 may completely fill one or more portions of the valve well 1304. In the illustrated embodiment, manifold ports 1354-3, 1354-4 of valve body 1350 may be aligned with the water input channel 1306 and water output channels 1312, respectively, such that flow 1388 enters the water input channel 1306 and exits the water output channel 1312. In various such embodiments, the outer surface 1351 of the valve body 1350 may block flow 1338 from accessing the balloon channel 1314. In some embodiments, the valve body 1350 may be vertically displaced such that the manifold ports 1354-1, 1354-2 are aligned with balloon channel 1314 and water input channel 1306, respectively. In some such embodiments, the outer surface 1351 of the valve body 1350 may block flow 1338 from accessing the water output channel 1312. In some embodiments, the outer surface 1351 of valve body 1350 (in conjunction with the valve body 1350 itself) may block flow 1388 from accessing the upper portion of the valve, which directs air flow.

In many embodiments, the outer surface 1351 of valve body 1350 may mate with one or more portions of the valve well to create a seal therebetween to block/control a flow. For example, the outer surface 1351 may block the flow 1338 from penetrating between the AW valve well 1304 and the valve body 1350. In such examples, this may prevent a portions of flow 1388 from being lost via balloon channel 1314. In some embodiments, channels may be used in conjunction with seals (e.g., an O-ring). In various embodiments, one or more portions of the primary control valve 1320 may be made of 3D printed metal or plastic. In some embodiments, one or more portions of the primary control valve 1320 may be constructed by drilling a central hole in a solid shaft with multiple radial holes drilled and certain portions of the central hole being plugged to create separate channels. In various embodiments, one or more channels described herein may include one or more of a vertical orientation, a horizontal orientation, a circumferential orientation, a spiral orientation, a diagonal orientation, and the like to control flow through a valve well.

Figure 14:
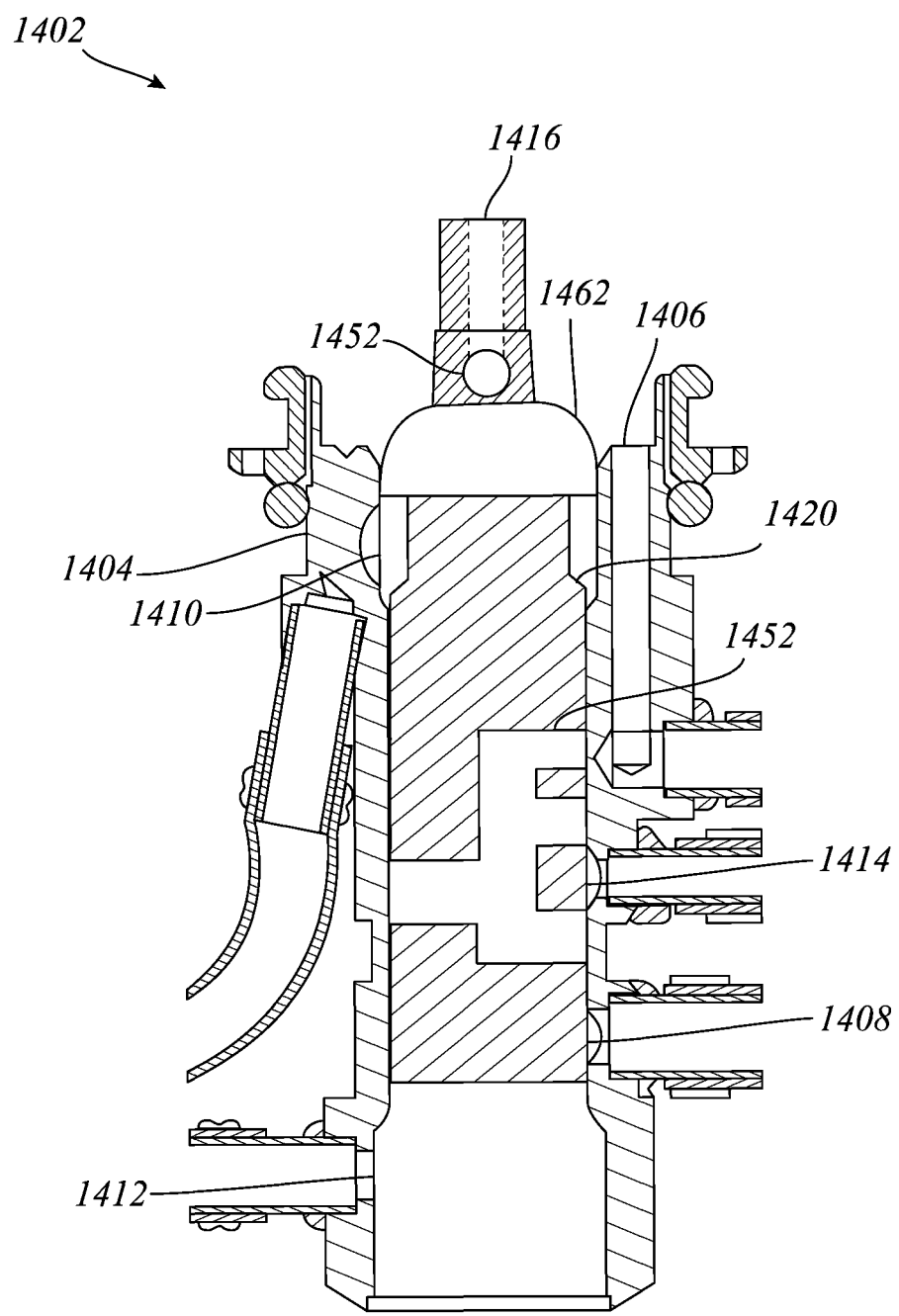
FIG. 14 illustrates various aspects of an exemplary AW valve assembly, according to one or more embodiments described herein.

FIG. 14 illustrates various aspects of an exemplary AW valve assembly 1402 in environment 1400, according to one or more embodiments described herein. In many embodiments, a cross section of one or more components may be illustrated in environment 1400. In some embodiments, one or more components of FIG. 14 may be the same or similar to one or more other components described herein. In environment 1400, the AW valve assembly 1402 may include primary control valve 1420 in conjunction with AW valve well 1404 and diaphragm switch 1462. In many embodiments, diaphragm switch 1462 may be included in a valve interface mechanism (e.g., as a biasing member and/or user interface member). In other embodiments, diaphragm switch 1462 may couple to the primary control valve 1420. In various embodiments, diaphragm switch 1462 may create a seal with one or more other components of AW valve assembly 1402, such as AW valve well 1404, one or more valves, and/or valve interface mechanisms.

AW valve assembly 1402 of environment 1400 may provide tactile feedback via a two spring setup. For instance, rigid components may contact each other to create tactile feedback. In some such embodiments, the contact may occur in an upper portion of the AW valve assembly 1402. In one or more embodiments described herein, diaphragm switch 1462 may create tactile feedback provided via an interface, (e.g., interface member), such as by inverting. In one or more embodiments, the diaphragm switch 1462 may comprise and/or operate as one or more biasing members. In some embodiments, diaphragm switch 1462 may bias the primary control valve in a specific position or state. Embodiments are not limited in this context.

In several embodiments, diaphragm switch 1462 may be configured to position the valve body of primary control valve 1420 in a first state when not compressed and in a second state when compressed. In some embodiments, the first state may include an open and/or noninverted position and the second state may include a sealed and/or inverted position. In one or more embodiments, primary control valve 1420 may include one or more air channels (e.g., manifold channel) that enables fluid to flow from the radial air hole 1452 and the air output channel 1410. In one or more such embodiments, the diaphragm switch 1462 may control the flow through the radial air hole 1452 and/or an opening to the one or more channels based on position. For example, when diaphragm switch 1462 inverts as the primary control valve 1420 moves downward, one or more flow openings located below the radial air hole 1452 (e.g., opposite side of the diaphragm switch 1462 may be revealed and/or unsealed.

In one or more embodiments, the diaphragm switch 1462 may route air, which is determined based on whether or not the atmospheric channel 1416 is sealed, such as with a finger. This may be a separate operation from those utilizing manifold channels 1452 and routing water. The water operations may be achieved by depressing the primary control valve 1420 to the first and second stops (e.g., water delivery state and balloon fill state, respectively).

In many embodiments, the AW valve assembly 1402 may be utilized in conjunction with one or more additional components. For example, a housing may couple with the lip of the AW valve well 1404. In another example, an air input valve, such as a radial seal, may be used to control flow through air input channel 1406. In many embodiments, the additional components may create a seal between the AW valve well 1404 and the primary control valve 1420. For example, the additional components may create a radial seal on the primary control valve 1420 between the radial air hole 1452 and the opening of the atmospheric channel 1416. In many such examples, the primary control valve 1420 may be able to slide up and down while maintaining the radial seal. In several embodiments, the additional components may create a sealed enclosure with the AW valve well 1404. In various embodiments, the primary control valve 1420 may extend out of the sealed enclosure.

In additional, or alternative embodiments, primary control valve 1420 may be configured to place water input channel 1408 in fluid communication with water output channel 1412 when in a noninverted state and place water input channel 1408 in fluid communication with balloon channel 1414 when in an inverted state. In several embodiments, the diaphragm may seal with the AW valve well 1404 to block the flow of air downward toward the air output channel 1410. On the other hand, the diaphragm switch 1462 may not block water flow to the atmospheric channel. Instead, the outer surface of the primary control valve 1420 may seal with one or more portions of AQ valve well 1404. In some embodiments, the diaphragm switch may create a seal with radial air hole 1452, such as to block flow to atmospheric channel 1416. In some such embodiments, the diaphragm switch 1462 may only create a seal with the radial air hole 1352 when either inverted or noninverted.

Figure 15A:
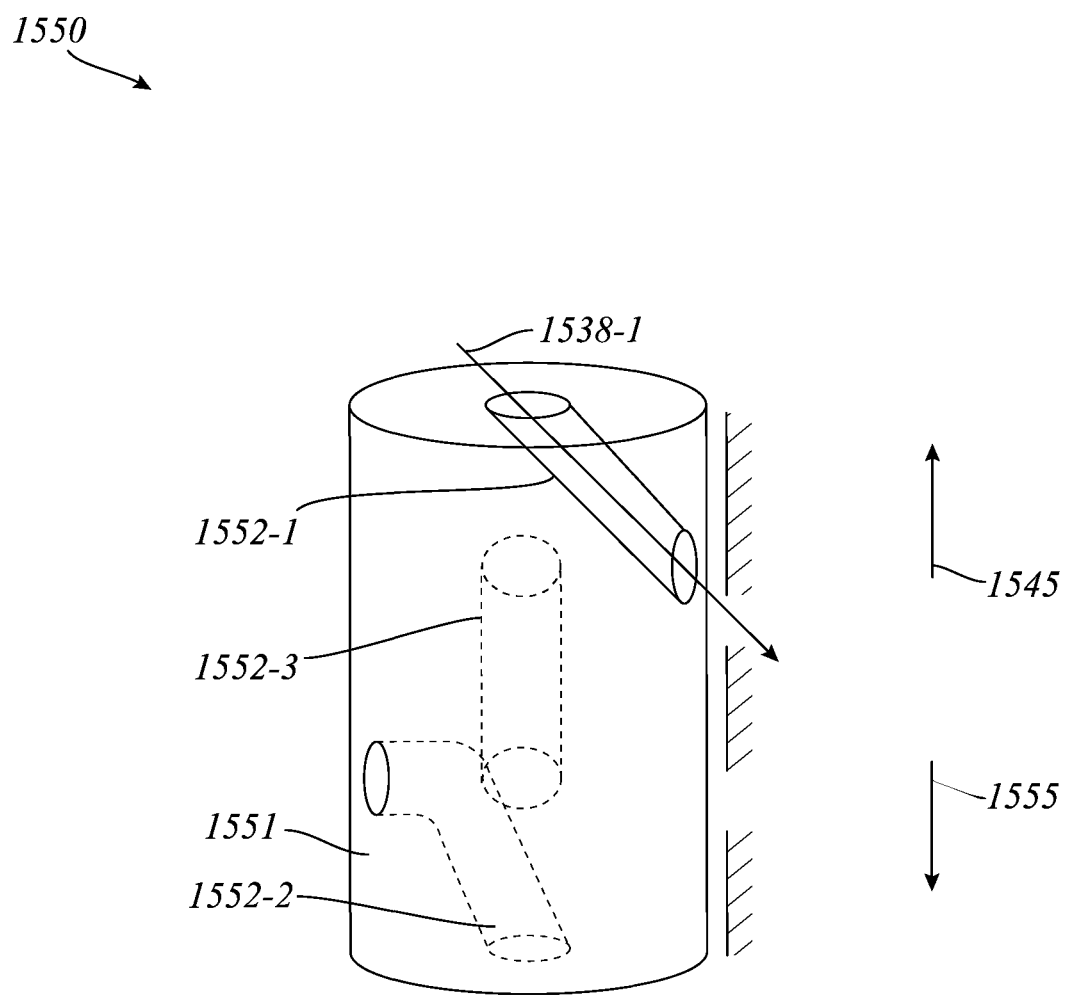
FIGS. 15A-15C illustrate various aspects of an exemplary valve body, according to one or more embodiments described herein.
Figure 15B:
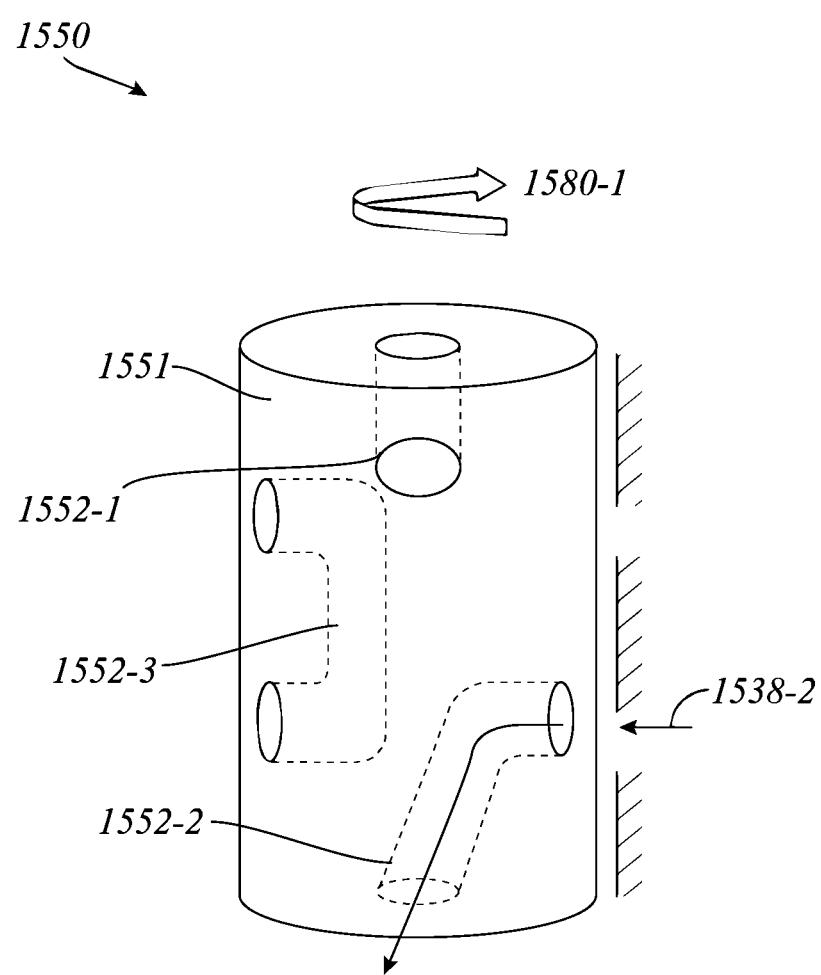
Figure 15C:
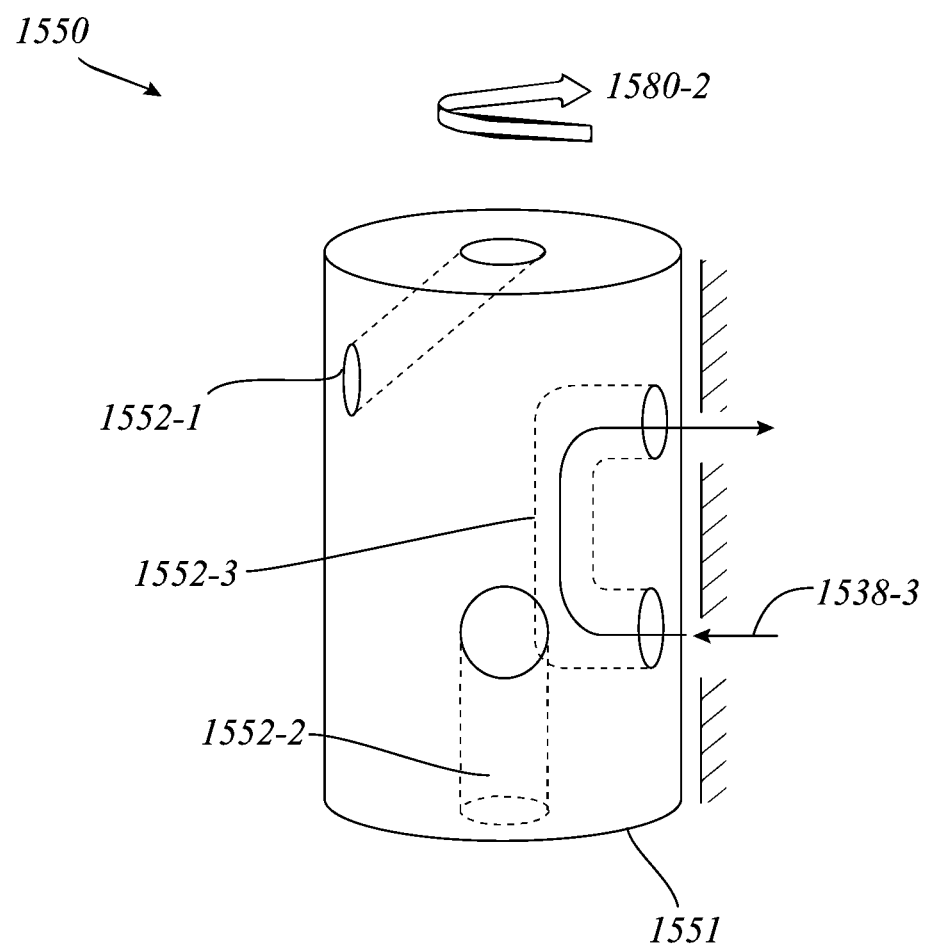

FIGS. 15A-15C illustrate various aspects of an exemplary valve body 1550 in environments 1500A, 1500B, 1500C, according to one or more embodiments described herein. In many embodiments, a cross section of one or more components may be illustrated in environments 1500A, 1500B, 1500C. In some embodiments, one or more components of FIGS. 15A-15C may be the same or similar to one or more other components described herein. Environments 1500A, 1500B, 1500C may include valve body 1550 with a top 1545, a bottom 1555, an outer surface 1551, and manifold channels 1552-1, 1552-2, 1552-3. In environment 1500A, valve body 1550 may be in a state where flow 1538-1 passes through manifold channel 1552-1. In environment 1500B, valve body 1550 may be in a state where flow 1538-2 passes through manifold channel 1552-2. In the illustrated embodiment, valve body 1550 may undergo a clockwise rotation 1580-1 to transition from flow 1538-1 to flow 1538-2. In environment 1500C, valve body 1550 may be in a state where flow 1538-3 passes through manifold channel 1552-3. In the illustrated embodiment, valve body 1550 may undergo a clockwise rotation 1580-2 to transition from flow 1538-2 to flow 1538-3. Embodiments are not limited in this context.

In various embodiments, valve bodies may include one or more channels to control flow through a valve well. In one or more embodiments, manifold channel 1552-1 may be associated with an air input channel of an AW valve assembly, manifold channel 1552-2 may be associated with a water input channel and a water output channel, and manifold channel 1552-3 may be associated with a water input channel and a balloon channel. In many embodiments, the valve body may utilize rotation to transition between different states. In many such embodiments, the valve interface mechanism may translate user input into rotation to transition between different states.

In some embodiments, a valve assembly may utilize four states. In a first state (e.g., air escape state), the valve body 1550 may block flow through air output channel with outer surface 1551. Additionally, or alternatively, the outer surface 1551 may block flow through one or more of a balloon channel, a water input channel, and a water output channel in the first state. Referring to environment 1500A, in a second state (e.g., air delivery state), the valve body 1550 may place the air output channel in fluid communication with the air input channel via manifold channel 1552-1 to facilitate flow 1538-1. Additionally, or alternatively, the outer surface 1551 may block flow through one or more of a balloon channel, a water input channel, and a water output channel in the second state. In many embodiments, a portion of the manifold channel 1552-1 (e.g., a manifold port) may be aligned with the air output channel in the second state. In various embodiments, a first rotation (e.g., a clockwise rotation) may transition the valve body 1550 from the first state to the second state.

Referring to environment 1500B, in a third state (e.g., water delivery state), the valve body 1550 may place the water input channel in fluid communication with water output channel via manifold channel 1552-2. Additionally, or alternatively, the outer surface 1551 may block flow through one or more of the balloon channel and air input channel in the third state. In many embodiments, a first portion of the manifold channel 1552-2 (e.g., a first manifold port) may be aligned with the water input channel and a second portion of the manifold channel (e.g., a second manifold port) may be aligned with the water output channel in the third state. In various embodiments, a second rotation (e.g., clockwise rotation 1580-1) may transition the valve body 1550 from the second state to the third state.

Referring to environment 1500C, in a fourth state (e.g., balloon state), the valve body 1550 may place the water input channel in fluid communication with the balloon channel via manifold channel 1552-3. Additionally, or alternatively, the outer surface 1551 may block flow through one or more of the water output channel and air input channel in the fourth state. In many embodiments, a first portion of the manifold channel 1552-3 (e.g., a first manifold port) may be aligned with the water input channel and a second portion of the manifold channel (e.g., a second manifold port) may be aligned with the balloon channel in the fourth state. In various embodiments, a third rotation (e.g., clockwise rotation 1580-2) may transition the valve body 1550 from the second state to the third state.

Figure 16:
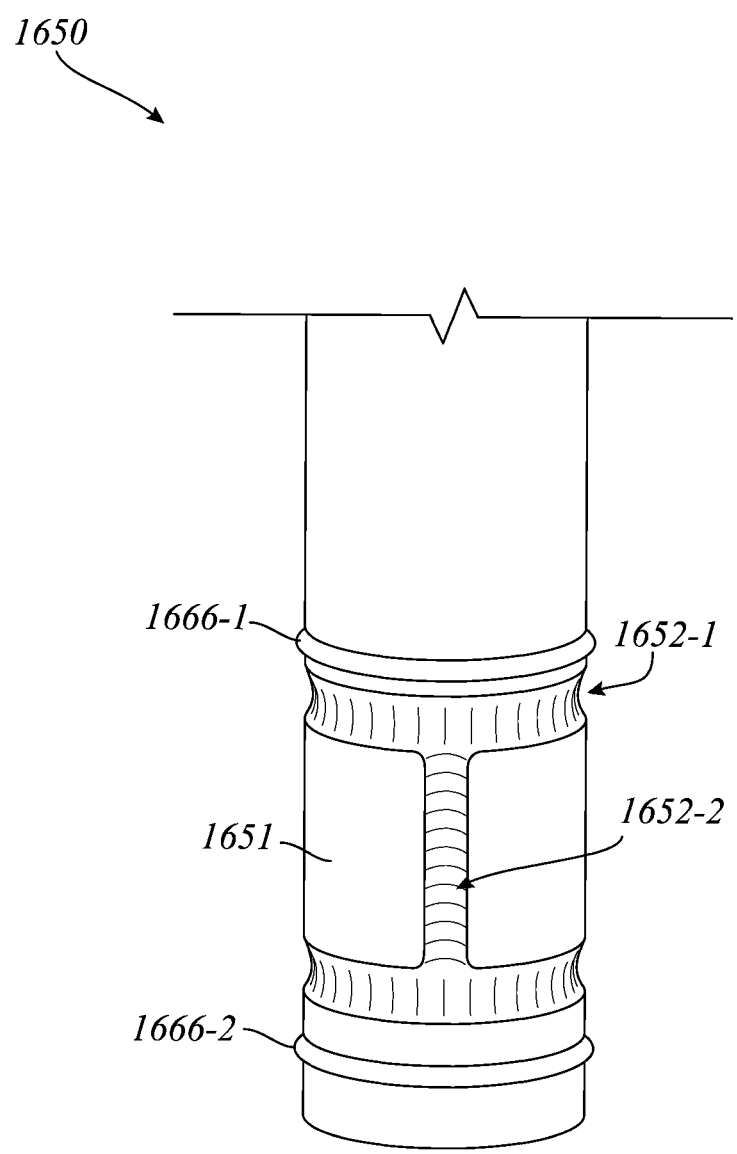
FIG. 16 illustrates various aspects of an exemplary valve body, according to one or more embodiments described herein.
Figure 17A:
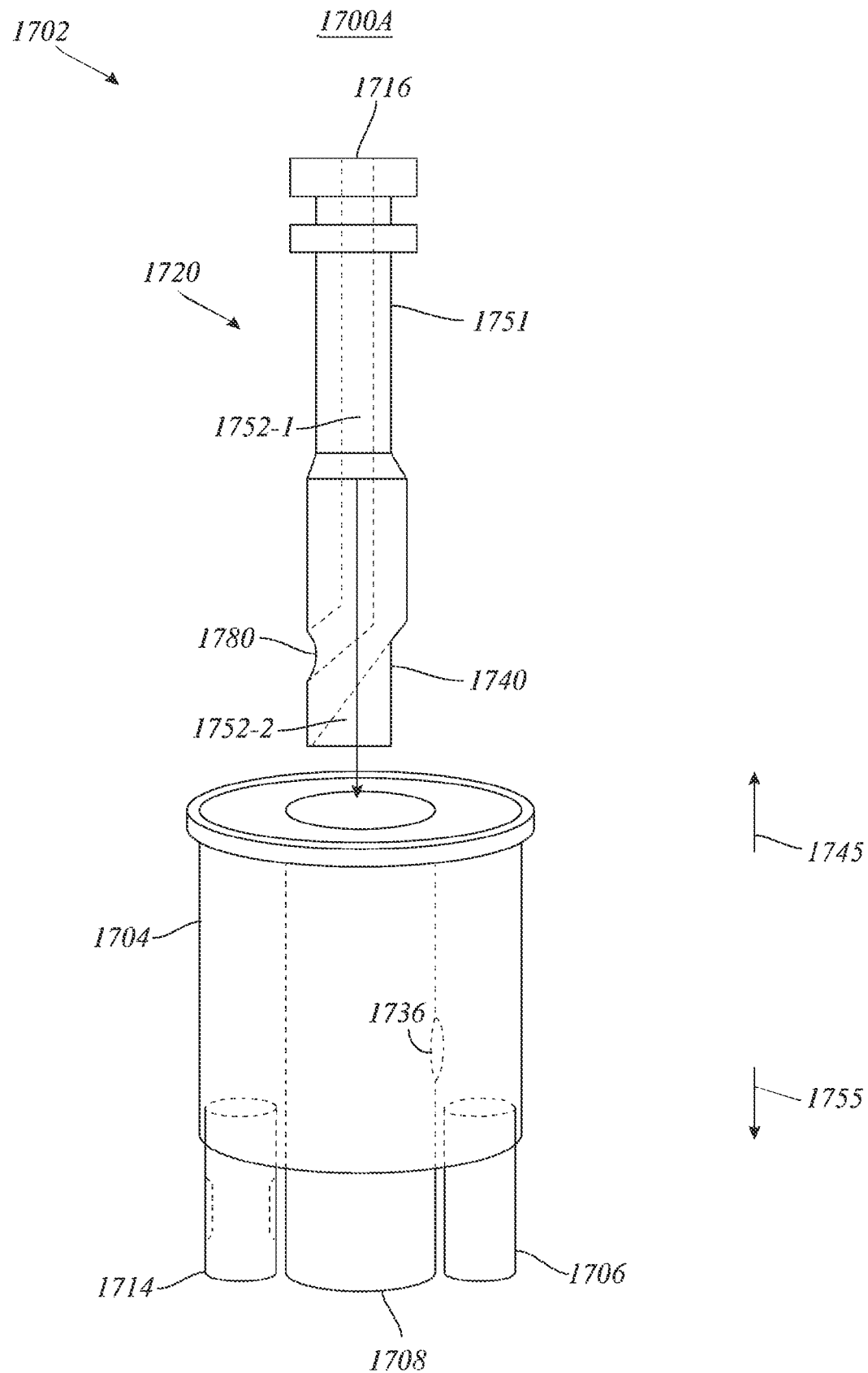
FIGS. 17A-17D illustrate various aspects of an exemplary suction valve assembly, according to one or more embodiments described herein.
Figure 17D:
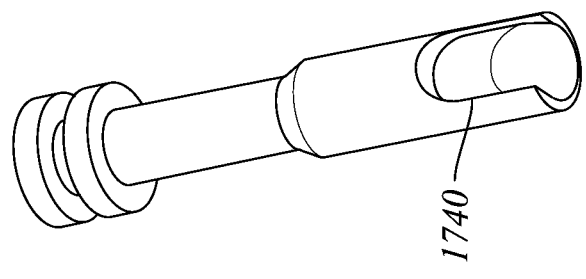
Figure 17C:
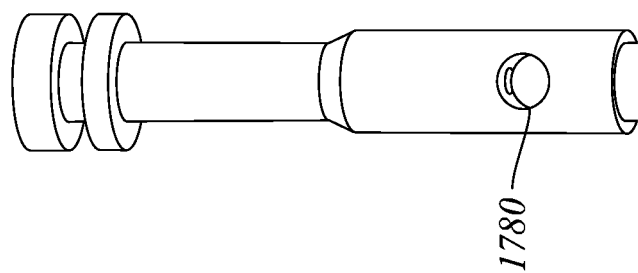
Figure 17B:
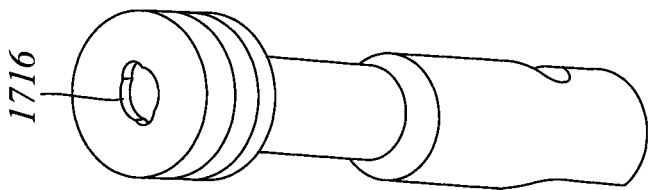

FIG. 16 illustrates various aspects of an exemplary valve body 1650 in environment 1600, according to one or more embodiments described herein. In many embodiments, a cross section of one or more components may be illustrated in environment 1600. In some embodiments, one or more components of FIG. 16 may be the same or similar to one or more other components described herein. In environment 1600, the valve body may include outer surface 1651, surface channels 1652-1, and O-rings 1666-1, 1666-2. In several embodiments described herein, one or more surface channels may be used to control flow through a valve body, such as in conjunction with manifold channels. In some embodiments, valve bodies may include features, such as grooves, slots, or holes, to receive/couple to a seal. In the illustrated embodiment, surface channel 1652-1 comprises a circumferential surface channel and surface channel 1652-2 comprising a vertical surface channel. In additional, or alternative, embodiments, one or more of diagonal channels, circumferential channels, vertical channels, spiral channels, and the like may be used. In several embodiments, one or more seals may be used to restrict flow to one or more channels in fluid communication. Embodiments are not limited in this context.

FIGS. 17A-17D illustrate various aspects of an exemplary suction valve assembly 1702 in environments 1700A, 1700B, 1700C, 1700D according to one or more embodiments described herein. In many embodiments, a cross section of one or more components may be illustrated in environments 1700A, 1700B, 1700C, 1700D. In some embodiments, one or more components of FIGS. 17A-17D may be the same or similar to one or more other components described herein. Environments 1700A, 1700B, 1700C, 1700D may include a working channel valve 1720 with an atmospheric channel 1716, an outer surface 1751, channels 1752-1, 1752-2, working channel access port 1740 and atmospheric access port 1780. Further, working channel valve 1720 may be oriented with a top 1745 and a bottom 1755. In environment 1700A, working channel valve 1720 is illustrated in conjunction with suction valve well 1704. Suction valve well 1704 may include balloon channel 1714, working channel 1708 with well radial hole 1736, and suction channel 1706. Further, suction valve well 1704 may be oriented with top 1745 and bottom 1755. Environments 1700B, 1700C, 1700D illustrate different perspective view of the working channel valve 1720. In one or more embodiments described herein, working channel valve 1720 may control flow through suction valve well 1704 via one or more rotational movements. In additional, or alternative embodiments, vertical movements may be used. Embodiments are not limited in this context.

In various embodiments, working channel valve 1720 may be inserted into the working channel 1708. In one or more embodiments, channel 1752-1 may place atmospheric access port 1780 in fluid communication with atmospheric channel 1716 and channel 1752-2 may place working channel access port 1740 in fluid communication with working channel 1708. In many embodiments, the working channel valve 1720 utilizes rotation to transition between different states. In many such embodiments, the valve interface mechanism may translate user input into rotation to transition between different states. For example, linear translation of a member with a helical boss interfacing with a component having a grove that the linear motion of the helix causes to rotate. In many examples, the second component may not translate with the first button press (e.g., moving to first stop), but the second component may translate with the second button press (e.g., moving to second stop).

In some embodiments, suction valve assembly 1702 may utilize three states. In a first state (e.g., atmospheric suction state), the working channel valve 1720 may place the atmospheric channel 1716 in fluid communication with suction channel 1706 via channel 1752-1. Additionally, or alternatively, the outer surface 1751 may block flow through working channel 1708. In many embodiments, the atmospheric access port 1780 may be aligned with the well radial hole 1736 in the first state.

In a second state (e.g., working channel suction state), the working channel valve 1720 may place the suction channel 1706 in fluid communication with working channel 1708 via channel 1752-2. Additionally, or alternatively, the outer surface 1751 may block flow through channel 1752-1. In many embodiments, the working channel access port 1740 may be aligned with the well radial hole 1736 in the second state. In several embodiments, the working channel valve may be rotated to transition from the first state to the second state.

In a third state (e.g., balloon channel suction state), the working channel valve 1720 may be moved downward to seal with the outer surface, thereby preventing fluid flow from the working channel. In some embodiments, the same movement can cause the hat (e.g., slide) to also move down, moving the balloon shaft down. In various embodiments, the working channel valve 1720 may be moved downward to place the suction channel 1706 in fluid communication with balloon channel 1714. Additionally, or alternatively, the outer surface 1751 may block flow through channel 1752-1 and/or channel 1752-2. As previously mentioned, the outer surface 1751 may be aligned with the well radial hole 1736 in the third state. In several embodiments, the working channel valve may be rotated and/or translated to transition from the second state to the third state.

The medical devices of the present disclosure are not limited, and may include a variety of medical devices for accessing body passageways, including, for example, duodenoscopes, catheters, ureteroscopes, bronchoscopes, colonoscopes, arthroscopes, cystoscopes, hysteroscopes, EUS endoscopes, and the like. In various embodiments, the valve assemblies, or components thereof, described herein may include one or more (e.g., as a single or set of units) of a mounting point, mechanical coupler, bearing, seal, O-ring, actuator, valve, diaphragm, gasket, housing, connector, structural member, manifold, ergonomic features (e.g., finger/thumb grooves, padding, grip, application of mechanical advantage, and the like), spring, bellow, cantilever biasing member, torsional biasing member, linear biasing member, flapper valve, skirt, fin, disc, channel, cavity, lumen, and the like. In many embodiments, one or more components described herein may be constructed utilizing a variety of devices, technologies and/or processes, such as three-dimensional (3D) printing, multi-axis computer numeric control (CNC) machines, additive manufacturing, subtractive manufacturing, injection molding, computer aided design (CAD) programs, path planning programs, machining, forging, casting, and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
   a valve set including a primary control valve, an air input valve, and an atmospheric valve, the primary control valve comprising a valve body with an outer surface and one or more manifold channels through the valve body configured to control flow between a water input channel, a water output channel, and a balloon channel of a valve well, the air input valve configured to control flow through an air input channel of the valve well, and the atmospheric valve configured to control flow through an atmospheric channel;
   a valve interface mechanism operable between a first state, a second state, a third state, and a fourth state, the first state comprising the valve set configured to place the air input channel in fluid communication with the atmospheric channel, the second state comprising the valve set configured to place the air input channel in fluid communication with the air output channel, the third state comprising the valve set configured to place the water input channel in fluid communication with the water output channel, and the fourth state comprising the valve set configured to place the water input channel in fluid communication with the balloon channel;
   wherein the outer surface of the valve body comprises first, second, third and fourth manifold ports in fluid communication via the one or more manifold channels, wherein the first and second manifold ports are configured to place the water input channel in fluid communication with the water output channel, and the third and fourth manifold ports are configured to place the water input channel in fluid communication with the balloon channel.

2. The medical device of claim 1, the valve interface mechanism,
   in the third state, configured to position a first portion of the one or more channels in fluid communication with the water input channel of the valve well and a second portion of the one or more channels in fluid communication with the water output channel.

3. The medical device of claim 2, the valve interface mechanism, in the third state, configured to position the outer surface of the valve body to block flow through the balloon channel.

4. The medical device of claim 2, the valve interface mechanism,
   in the fourth state, configured to position a third portion of the one or more channels in fluid communication with the water input channel of the valve well and a fourth portion of the one or more channels in fluid communication with the balloon channel.

5. The medical device of claim 1, the valve interface mechanism configured to vertically displace the valve body to transition between one or more of the first state and the second state, the second state and the third state, and the third state and the fourth state.

6. The medical device of claim 1, the outer surface of the valve body comprising one or more seals or one or more grooves configured to receive one or more seals.

* * * * *